(12) United States Patent
Hu

(10) Patent No.: US 7,390,781 B2
(45) Date of Patent: *Jun. 24, 2008

(54) METHODS OF USING TRUNCATED GLIAL CELL LINE-DERIVED NEUROTROPHIC FACTOR

(75) Inventor: Shaw-Fen Sylvia Hu, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 362 days.

This patent is subject to a terminal disclaimer.

(21) Appl. No.: 10/753,592

(22) Filed: Jan. 7, 2004

(65) Prior Publication Data

US 2004/0127419 A1 Jul. 1, 2004

Related U.S. Application Data

(60) Continuation of application No. 09/687,984, filed on Oct. 13, 2000, now abandoned, which is a division of application No. 08/535,681, filed on Sep. 28, 1995, now Pat. No. 6,184,200.

(51) Int. Cl.
*A61K 38/18* (2006.01)
*C07K 14/475* (2006.01)

(52) U.S. Cl. ............................. 514/2; 514/12; 530/300; 530/350; 530/399

(58) Field of Classification Search ............. None
See application file for complete search history.

(56) References Cited

U.S. PATENT DOCUMENTS

| | | | |
|---|---|---|---|
| 4,419,446 A | 12/1983 | Howley et al. | |
| 4,518,584 A | 5/1985 | Mark et al. | |
| 4,892,538 A | 1/1990 | Aebischer et al. | |
| 5,011,472 A | 4/1991 | Aebischer et al. | |
| 5,106,627 A | 4/1992 | Aebischer et al. | |
| 5,202,428 A | 4/1993 | Schubert | |
| 5,252,714 A | 10/1993 | Harris et al. | |
| 5,272,071 A | 12/1993 | Chappel | |
| 5,641,749 A * | 6/1997 | Yan et al. ..................... | 514/12 |
| 5,641,750 A * | 6/1997 | Louis ........................... | 514/12 |
| 5,731,284 A * | 3/1998 | Williams ....................... | 514/8 |
| 5,733,875 A * | 3/1998 | Martin .......................... | 514/12 |
| 5,741,778 A * | 4/1998 | Martin et al. .................. | 514/12 |
| 5,837,681 A * | 11/1998 | Magal ........................... | 514/12 |
| 5,929,041 A * | 7/1999 | Magal ........................... | 514/44 |
| 6,184,200 B1 | 2/2001 | Hu | |
| 6,245,330 B1 | 6/2001 | Horellou et al. | |
| 2004/0214776 A1 | 10/2004 | Hu | |
| 2004/0254114 A1 | 12/2004 | Hu | |

FOREIGN PATENT DOCUMENTS

| | | |
|---|---|---|
| EP | 154 316 | 3/1985 |
| EP | 401 384 | 12/1989 |
| EP | 398 753 | 5/1990 |
| EP | 423 980 | 4/1991 |
| WO | WO91/03568 | 3/1991 |
| WO | WO91/10425 | 7/1991 |
| WO | WO91/10470 | 7/1991 |
| WO | WO93/06116 | 4/1993 |
| WO | WO95/17203 | 6/1995 |
| WO | WO95/26408 | 10/1995 |
| WO | WO 97/08196 | 3/1997 |

OTHER PUBLICATIONS

Hankins et al. *Documenta ophthalmologies Advances in ophthalmology*, vol. 86, pp. 325-334, 1994.*
Matsuaka et al. *Acta oto-laryngologica. Supplementary*, vol. 419, pp. 62-70, 1984.*
Rudinger, In *Peptide Hormones*, J. A. Parsons, ed. University Park Press, Baltimore, 1976.*
Varon et al., (1978) *Ann. Rev. Neuroscience* 1:327-361.
Thoenen et al., (1985) *Science* 229:238-242.
Rich et al., (1987) *J. Neurocytol.* 16:261-268.
Otto et al., (1987) *Neurosci. Lett.* 83:156-160.
Hamburger et al., (1984) *J. Neurosci.* 4:767-774.
Apfel et al., (1991) *Ann. Neurol.* 29:87-90.
Hofer et al., (1988) *Nature* 331:261-262.
Lin et al., (1989) *Science* 246:1023-1025.
Fausset et al., (1991) *Electrophoresis* 12:22-27.
Dayhoff, (1972) *Atlas of Protein Sequence and Structure* 5:124.
Cunningham et al., (1989) *Science* 244:1081-1085.
Francis, (1992) *Focus on Growth Factors* 3(2):4-10.
Malik et al., (1992) *Exp. Hematol.* 20:1028-1035.
Chamow et al., (1994) *Bioconjugate Chem.* 5:133-140.
Maniatis et al., (1982) *Molecular Cloning* (A Laboratory Manual), 387-389.
Engels et al., (1989) *Chem. Intl. Ed.*, 28:716-734.

(Continued)

*Primary Examiner*—Christina Chan
*Assistant Examiner*—Stephen Gucker
(74) *Attorney, Agent, or Firm*—Lawrence B. Bugaisky

(57) ABSTRACT

Disclosed are novel proteins, referred to as truncated glial cell line-derived neurotrophic factor (truncated GDNF) proteins, that promote dopamine uptake by dopaminergic cells and promote the survival of nerve cells. Also disclosed are processes for obtaining the truncated GDNF proteins by recombinant genetic engineering techniques.

20 Claims, 9 Drawing Sheets

OTHER PUBLICATIONS

Wells et al., (1985) *Gene* 34:315-323.
Urlaub et al., (1980) *Proc. Natl. Acad. Sci.*, USA 77(7):4216-4220.
Takebe et al., (1988) *Mol. Cell. Biol.* 8(1):466-472.
Sambrook, (1981) *Nature* 293:620-625.
Kaufman et al., (1985) *Mol. Cell. Biol.* 5(7):1750-1759.
Kucherlapati, (1989) *Prog. in Nucl. Acid Res. and Mol. Biol.* 36:301-310.
Thomas et al., (1986) *Cell* 44:419-428.
Thomas et al., (1987) *Cell* 51:503-512.
Doetschman et al., (1988) *Proc. Natl. Acad. Sci.* 85:8583-8587.
Doetschman et al., (1987) *Nature* 330:576-578.
Winn et al., (1991) *Exper. Neurol.* 113:322-329.
Aebischer et al., (1991) *Exper. Neurol.* 111:269-275.
Tresco et al., (1992) *ASAIO* 38:17-23.
Okayama et al., (1983) *Mol. Cell. Biol.* 3:280-289.
Goodwin et al. (1983) *Nucleic Acids Res.* 11:6873-6882.
Gasser et al. (1982) *Proc. Natl. Acad. Sci.* 79:6522-6526.
Erlich, Ed., (1989) *PCR Technology, Principles and Applications for DNA Amplification*, Chapter 6:61-70.
Louis et al., (1992) *J. Pharmacol. Exp. Therap.* 262:1274-1283.
Louis et al., (1993) *Science* 259:689-692.
Lin et al., (1994) *J. Neurochem.* 63(2): 758-768.
Friedman et al., (1987) *Neuro. Sci. Lett.* 79:65-72.
Schubert et al., (1974) *Nature* 249:224-227.
Lin et al., (1993) *Science* 260:1130-1132.
Bohn et al., (1989) *Soc. Neurosci. Abs.* 15:277.
Schaar, et al. (1994), 'Multiple Astrocyte Transcripts Encode Nigral Trophic Factors in Rat and Human', *Exp. Neurology* 130:387-393.
Zang, T.J. et al. "The Biological Activity of N-Terminally Truncated Forms of GDNF on Cultured Mesencephalic Dopaminergic Neurons," *Society for Neuroscience*, vol. 22(3):1955, (1996).
Barnett, M.W. et al., "Signally by glial cell line-derived neurotrophic factor (GDNF) requires heparan sulphate glycosaminoglycan," *J. of Cell Sci.*, 115:4495-4503, (2002).
Fry, E. J. "Central Nervous System Regeration: Mission Impossible?," *Clinical and Experimental Pharmacology and Physiology* 28:253-258, (2001).
Jackowski, A., "Neural injury repair: hope for the future as barriers to effective CNS regeneration become clearer," *British Journal of Neruosurgery*, 9:303-317, (1995).
Rickard, S. M., "The binding of human glial cell line-derived neurotrophic factor to heparin and heparan sulfate: importance of 2-O-sulfate groups and effect on its interaction with its receptor, GFR• 1," *Glycobiology*, vol. 13(6):419-426, (2003).
Sariola, H., "Novel functions and signalling pathways for GDNF," *J. of Cell Sci.*, 116:3855-3862, (2003).

* cited by examiner

FIG. 1

Mature Human GDNF

| | | | | | | | | | | | | | |
|---|---|---|---|---|---|---|---|---|---|---|---|---|---|
| TCA | CCA | GAT | AAA | CAA | ATG | GCA | GTG | CTT | CCT | AGA | AGA | GAG | CGG | AAT |
| Ser | Pro | Asp | Lys | Gln | Met | Ala | Val | Leu | Pro | Arg | Arg | Glu | Arg | Asn |
| | | | | 5 | | | | | 10 | | | | | 15 |

```
TCA CCA GAT AAA CAA ATG GCA GTG CTT CCT AGA AGA GAG CGG AAT
Ser Pro Asp Lys Gln Met Ala Val Leu Pro Arg Arg Glu Arg Asn
              5                  10                      15

CGG CAG GCT GCA GCT GCC AAC CCA GAG AAT TCC AGA GGA AAA GGT
Arg Gln Ala Ala Ala Ala Asn Pro Glu Asn Ser Arg Gly Lys Gly
             20                  25                      30

CGG AGA GGC CAG AGG GGC AAA AAC CGG GGT TGT GTC TTA ACT GCA
Arg Arg Gly Gln Arg Gly Lys Asn Arg Gly Cys Val Leu Thr Ala
             35                  40                      45

ATA CAT TTA AAT GTC ACT GAC TTG GGT CTG GGC TAT GAA ACC AAG
Ile His Leu Asn Val Thr Asp Leu Gly Leu Gly Tyr Glu Thr Lys
             50                  55                      60

GAG GAA CTG ATT TTT AGG TAC TGC AGC GGC TCT TGC GAT GCA GCT
Glu Glu Leu Ile Phe Arg Tyr Cys Ser Gly Ser Cys Asp Ala Ala
             65                  70                      75

GAG ACA ACG TAC GAC AAA ATA TTG AAA AAC TTA TCC AGA AAT AGA
Glu Thr Thr Tyr Asp Lys Ile Leu Lys Asn Leu Ser Arg Asn Arg
             80                  85                      90

AGG CTG GTG AGT GAC AAA GTA GGG CAG GCA TGT TGC AGA CCC ATC
Arg Leu Val Ser Asp Lys Val Gly Gln Ala Cys Cys Arg Pro Ile
             95                  100                     105

GCC TTT GAT GAT GAC CTG TCG TTT TTA GAT GAT AAC CTG GTT TAC
Ala Phe Asp Asp Asp Leu Ser Phe Leu Asp Asp Asn Leu Val Tyr
             110                 115                     120

CAT ATT CTA AGA AAG CAT TCC GCT AAA AGG TGT GGA TGT ATC
His Ile Leu Arg Lys His Ser Ala Lys Arg Cys Gly Cys Ile
             125                 130
```

FIG.3A metGDNF Degenerate DNA Sequence

```
                                          B
                        N                 s
                        d                 p
                        e                 E
                        I                 I
        CATATGTCTCCGGATAAACAAATGGCTGTTCTTCCAC
  1  ---------+---------+---------+---------+---------+---------+  60
                 MetSer

E
                 N                     c
                 o                     o
                 t                     R
                 I                     I
        GTCGTGAACGTAACCGTCAGGCGGCCGCTGCTAACCCGGAGAATTCCCGTGGTAAAGGTC
 61  ---------+---------+---------+---------+---------+---------+ 120

S
                            a
                            c
                            I
                            I
        GTCGTGGTCAGCGTGGTAAAAACCGCGGTTGCGTTCTGACCGCTATCCACCTGAACGTTA
121  ---------+---------+---------+---------+---------+---------+ 180

P
           s
           h
           A
           I
        CCGACCTGGGTCTCGGTTACGAAACCAAAGAAGAATTAATCTTCCGTTACTGCTCCGGTT
181  ---------+---------+---------+---------+---------+---------+ 240
```

FIG.3B

```
                              S
                              u
                              n
                              I
         CCTGCGACGCTGCTGAAACCACGTACGACAAAATCCTGAAAAACCTGTCCCGTAACCGTC
    241  ---------+---------+---------+---------+---------+---------+ 300

E
                      H                                             a
                      i                                             m
                      n                                             1
                      d                          P                  1
                      I                          v                  0
                      I                          u                  5
                      I                          I                  I
         GTCTGGTTTCCGACAAAGTTGGTCAAGCTTGCTGCCGTCCGATCGCTTTCGACGACGACC
    301  ---------+---------+---------+---------+---------+---------+ 360

TGTCCTTCCTGGACGACAACCTGGTTTACCACATCCTGCGTAAACACTCCGCTAAGCGTT
    361  ---------+---------+---------+---------+---------+---------+ 420

B
                      a
                      m
                      H
                      I
         GCGGTTGCATCTAAGGATCC
    421  ---------+---------+ 440
```

FIG.4 metGDNF Degenerate DNA Sequence

```
                                             N
                                             d
                                             e
                                             I
                              CATATGAGCCCGGACAAACAG
  1  ---------+---------+---------+---------+---------+---------+  60
                                             MetSer

ATGGCAGTACTTCCACGTCGTGAACGTAATCGCCAGGCAGCAGCTGCAAACCCGGAAAAC
 61  ---------+---------+---------+---------+---------+---------+ 120

TCCCGTGGTAAAGGTCGCCGTGGCCAGCGCGGCAAAAACCGTGGTTGTGTTCTGACTGCA
121  ---------+---------+---------+---------+---------+---------+ 180

P
                s
                h
                A
                I
     ATCCACCTGAACGTTACTGACCTGGGTCTGGGCTACGAAACCAAAGAAGAACTGATCTTC
181  ---------+---------+---------+---------+---------+---------+ 240

P
            s
            t
            I
     CGCTACTGCAGCGGCTCTTGCGACGCAGCTGAAACCACTTACGACAAAATCCTGAAAAAC
241  ---------+---------+---------+---------+---------+---------+ 300

P
                                                         v
                                                         u
                                                         I
     CTGTCCCGTAACCGCCGTCTGGTAAGCGACAAAGTAGGTCAGGCATGCTGCCGTCCGATC
301  ---------+---------+---------+---------+---------+---------+ 360

B
           s
           m
           I
     GCATTCGACGATGACCTGAGCTTCCTGGATGACAACCTGGTTTACCACATCCTGCGTAAA
361  ---------+---------+---------+---------+---------+---------+ 420

B
                        a
                        m
                        H
                        I
     CACTCCGCTAAACGCTGCGGTTGCATCTAAGGATCC
421  ---------+---------+---------+------ 456
```

FIG.5

[Pro$^{23}$-Lys$^{37}$ΔAsn$^{37}$-Ile$^{134}$] Truncated GDNF Protein

```
     ATGTCCCCAGAAAATTCTCGTGGTAAAGGTCGTCGTGGTCAGCGTGGTAATAACCGCGGT
 21  ----------+---------+---------+---------+---------+---------+  80
      M  S  P  E  N  S  R  G  K  G  R  R  G  Q  R  G  N  N  R  G

TGCGTTCTGACCGCTATCCACCTGAACGTTACCGACCTGGGTCTCGGTTACGAAACCAAA
 81  ----------+---------+---------+---------+---------+---------+  140
      C  V  L  T  A  I  H  L  N  V  T  D  L  G  L  G  Y  E  T  K

GAAGAATTAATCTTCCGTTACTGCTCCGGTTCCTGCGACGCTGCTGAAACCACGTACGAC
141  ----------+---------+---------+---------+---------+---------+  200
      E  E  L  I  F  R  Y  C  S  G  S  C  D  A  A  E  T  T  Y  D

AAAATCCTGAAAAACCTGTCCCGTAACCGTCGTCTGGTTTCCGACAAAGTTGGTCAAGCT
201  ----------+---------+---------+---------+---------+---------+  260
      K  I  L  K  N  L  S  R  N  R  R  L  V  S  D  K  V  G  Q  A

TGCTGCCGTCCGATCGCTTTCGACGACGACCTGTCCTTCCTGGACGACAACCTGGTTTAC
261  ----------+---------+---------+---------+---------+---------+  320
      C  C  R  P  I  A  F  D  D  D  L  S  F  L  D  D  N  L  V  Y

CACATCCTGCGTAAACACTCCGCTAAGCGTTGCGGTTGCATCTAA
321  ----------+---------+---------+---------+-----
      H  I  L  R  K  H  S  A  K  R  C  G  C  I  *
```

FIG.6

[Arg$^{32}$-Ile$^{134}$] Truncated GDNF Protein

```
     ATGCGTGGTCAACGTGGTAAAAACCGCGGTTGCGTTCTGACTGCAATCCACCTGAACGTT
 41  ---------+---------+---------+---------+---------+---------+ 100
      M  R  G  Q  R  G  K  N  R  G  C  V  L  T  A  I  H  L  N  V

ACTGACCTGGGTCTGGGCTACGAAACCAAAGAAGAACTGATCTTCCGCTACTGCAGCGGC
101  ---------+---------+---------+---------+---------+---------+ 160
      T  D  L  G  L  G  Y  E  T  K  E  E  L  I  F  R  Y  C  S  G

TCTTGCGACGCAGCTGAAACCACTTACGACAAAATCCTGAAAAACCTGTCCCGTAACCGC
161  ---------+---------+---------+---------+---------+---------+ 220
      S  C  D  A  A  E  T  T  Y  D  K  I  L  K  N  L  S  R  N  R

CGTCTGGTAAGCGACAAAGTAGGTCAGGCATGCTGCCGTCCGATCGCATTCGACGATGAC
221  ---------+---------+---------+---------+---------+---------+ 280
      R  L  V  S  D  K  V  G  Q  A  C  C  R  P  I  A  F  D  D  D

CTGAGCTTCCTGGATGACAACCTGGTTTACCACATCCTGCGTAAACACTCCGCTAAACGC
281  ---------+---------+---------+---------+---------+---------+ 340
      L  S  F  L  D  D  N  L  V  Y  H  I  L  R  K  H  S  A  K  R

TGCGGTTGCATCTAA
341  ---------+----- 355
      C  G  C  I  *
```

FIG. 7

[Gly³³-Ile¹³⁴] Truncated GDNF Protein

```
     ATGGGTCAACGTGGTAAAAACCGTGGTTGTGTTCTGACTGCAATCCACCTGAACGTTACT
 41  ---------+---------+---------+---------+---------+---------+ 100
      M  G  Q  R  G  K  N  R  G  C  V  L  T  A  I  H  L  N  V  T

GACCTGGGTCTGGGCTACGAAACCAAAGAAGAACTGATCTTCCGCTACTGCAGCGGCTCT
101  ---------+---------+---------+---------+---------+---------+ 160
      D  L  G  L  G  Y  E  T  K  E  E  L  I  F  R  Y  C  S  G  S

TGCGACGCAGCTGAAACCACTTACGACAAAATCCTGAAAAACCTGTCCCGTAACCGCCGT
161  ---------+---------+---------+---------+---------+---------+ 220
      C  D  A  A  E  T  T  Y  D  K  I  L  K  N  L  S  R  N  R  R

CTGGTAAGCGACAAAGTAGGTCAGGCATGCTGCCGTCCGATCGCATTCGACGATGACCTG
221  ---------+---------+---------+---------+---------+---------+ 280
      L  V  S  D  K  V  G  Q  A  C  C  R  P  I  A  F  D  D  D  L

AGCTTCCTGGATGACAACCTGGTTTACCACATCCTGCGTAAACACTCCGCTAAACGCTGC
281  ---------+---------+---------+---------+---------+---------+ 340
      S  F  L  D  D  N  L  V  Y  H  I  L  R  K  H  S  A  K  R  C

GGTTGCATCTAA
341  ---------+-- 352
      G  C  I  *
```

FIG. 8

Comparison of Protein Sequences

```
                                                                    50
    GDNF  MSPDKQMAVL  PRRERNRQAA  AANPENSRGK  GRRGQRGKNR  GCVLTAIHLN

-31 GDNF  ..........  ..........  ..........  .MRGQRGKNR  GCVLTAIHLN

-32 GDNF  ..........  ..........  ..........  ..MGQRGKNR  GCVLTAIHLN

-22 GDNF  ..........  ..........  .MSPENSRGK  GRRGQRGNNR  GCVLTAIHLN 51                                                       100
    GDNF  VTDLGLGYET  KEELIFRYCS  GSCDAAETTY  DKILKNLSRN  RRLVSDKVGQ

-31 GDNF  VTDLGLGYET  KEELIFRYCS  GSCDAAETTY  DKILKNLSRN  RRLVSDKVGQ

-32 GDNF  VTDLGLGYET  KEELIFRYCS  GSCDAAETTY  DKILKNLSRN  RRLVSDKVGQ

-22 GDNF  VTDLGLGYET  KEELIFRYCS  GSCDAAETTY  DKILKNLSRN  RRLVSDKVGQ 101                               135
    GDNF  ACCRPIAFDD  DLSFLDDNLV  YHILRKHSAK  RCGCI

-31 GDNF  ACCRPIAFDD  DLSFLDDNLV  YHILRKHSAK  RCGCI

-32 GDNF  ACCRPIAFDD  DLSFLDDNLV  YHILRKHSAK  RCGCI

-22 GDNF  ACCRPIAFDD  DLSFLDDNLV  YHILRKHSAK  RCGCI
```

METHODS OF USING TRUNCATED GLIAL CELL LINE-DERIVED NEUROTROPHIC FACTOR

This application is a continuation of application Ser. No. 09/687,984, filed Oct. 13, 2000, now abandoned, which is a divisional of application Ser. No. 08/535,681, filed Sept. 28, 1995, issued as U.S. Pat. No. 6,184,200, which are hereby incorporated by reference.

FIELD OF THE INVENTION

In general, the present invention relates to proteins, referred to herein as glial cell line-derived neurotrophic factors (also referred to as glial derived neurotrophic factor or GDNF), that are characterized by the ability to promote dopamine uptake by dopaminergic neurons and support the survival of the neurons that die in Parkinson's Disease. The present invention more specifically relates to a novel truncated GDNF proteins.

BACKGROUND OF THE INVENTION

Neurotrophic factors are proteins, found in the nervous system or in non-nerve tissues innervated by the nervous system, whose function is to promote the survival and maintain the phenotypic differentiation of nerve and/or glial cells (Varon et al., *Ann. Rev. Neuroscience* 1:327, 1979; Thoenen et al., *Science* 229:238, 1985). Because of this physiological role, neurotrophic factors are useful in treating the degeneration of nerve cells and the loss of differentiated function that occurs in a variety of neurodegenerative diseases.

In order for a particular neurotrophic factor to be potentially useful in treating nerve damage, the class or classes of damaged nerve cells must be responsive to the factor. Different neurotrophic factors typically affect distinctly different classes of nerve cells. Therefore, it is advantageous to have on hand a variety of different neurotrophic factors to treat each of the classes of damaged neurons that may occur with different forms of disease or injury.

Neurotrophic factors can protect responsive neurons against a variety of unrelated insults. For example, nerve growth factor (NGF) will rescue a significant portion of sensory neurons from death caused by cutting their axonal processes (Rich et al., *J. Neurocytol* 16:261, 1987; Otto et al., *J. Neurosci.* 83:156, 1987), from ontogenetic death during embryonic development (Hamburger et al., *J. Neurosci.* 4:767, 1984), and from damage caused by the administration of taxol or cisplatin (Apfel et al., *Ann. Neurol.* 29: 87, 1991). This apparent generality of protection has led to the concept that if a neurotrophic factor protects responsive neurons against experimental damage, it may be useful in treating diseases that involve damage to those neurons in patients, even though the etiology may be unknown.

A given neurotrophic factor, in addition to having the correct neuronal specificity, must be available in sufficient quantity to be used as a pharmaceutical treatment. Since neurotrophic factors are typically present in small amounts in tissues (e.g., Hofer and Barde *Nature* 331:261, 1988; Lin et al., *Science* 246:1023, 1989), it would be inconvenient to prepare pharmaceutical quantities of neurotrophic factors directly from animal tissues. As an alternative, it is desirable to use a recombinant expression system to produce the desired protein.

Lin et al. previously described a method for screening biological samples for neurotrophic activity on the embryonic precursors of the *substantia nigra* dopaminergic neurons (see U.S. patent application Ser. No. 08/182,183 filed May 23, 1994 and its parent applications; PCT/US92/07888 filed Sep. 17, 1992 (WO 93/06116); and European Patent Application No. 92921022.7 (Publication No. EP 610 254); the disclosures of which are hereby incorporated by reference). This bioassay is useful in identifying neurotrophic factors which may be used in treating Parkinson's disease (Friedman et al., *Neuro. Sci. Lett.* 79:65-72, 1987) as the disease is characterized by the degeneration of dopaminergic neurons in the midbrain that innervate the striatum.

Lin et al. further described the characterization of a new neurotrophic factor that was purified from one such source, the conditioned culture medium from a glioblastoma cell line, B49 (Schubert et al., *Nature* 249:224-27, 1974). The conditioned medium from this cell line was previously reported to contain dopaminergic neurotrophic activity (Bohn et al., *Soc. Neurosci. Abs.* 15:277, 1989). Prior to the disclosure of Lin et al., glial cell line-derived neurotrophic factor (GDNF) had not been identified as a discrete biologically active substance or isolated as a substantially pure protein. In addition, Lin et al. described processes for cloning human genes encoding GDNF, the nucleic acid sequence of the human genes that encode GDNF and the amino acid sequences of the GDNF protein. The GDNF gene was subcloned into an expression vector, and the vector was used to express biologically active GDNF. The GDNF protein is a homodimer composed of two 134 amino acid, 22 kDa, subunits joined by disulfide bond. The description further included the use of GDNF for preventing and treating nerve damage and nerve related diseases such as Parkinson's disease.

GDNF therapy is helpful in the treatment of nerve damage caused by conditions that compromise the survival and/or proper function of one or more types of nerve cells. Such nerve damage may occur from a wide variety of different causes. Nerve damage may occur to one or more types of nerve cells by: (1) physical injury, which causes the degeneration of the axonal processes and/or nerve cell bodies near the site of injury; (2) temporary or permanent cessation of blood flow to parts of the nervous system, as in stroke; (3) intentional or accidental exposure to neurotoxins, such as chemotherapeutic agents (e.g., cisplatinum) for the treatment of cancer or dideoxycytidine (ddC) for the treatment of AIDS; (4) chronic metabolic diseases, such as diabetes or renal dysfunction; or (5) neurodegenerative diseases such as Parkinson's disease, Alzheimer's disease, and Amyotrophic Lateral Sclerosis (ALS), which result from the degeneration of specific neuronal populations.

GDNF therapy could be particularly helpful in the treatment of neurodegenerative conditions involving the degeneration of the dopaminergic neurons of the *substantia nigra*, such as Parkinson's disease. The only current treatments for Parkinson's disease are palliative, aiming at increasing dopamine levels in the striatum. The expected impact of GDNF therapy is not simply to produce an increase in the dopaminergic neurotransmission at the dopaminergic nerve terminals in the striatum (which will result in a relief of the symptoms), but also to slow down, or even stop, the progression of the degenerative processes and to repair the damaged nigrostriatal pathway and restore its function. GDNF may also be used in treating other forms of damage to or improper function of dopaminergic nerve cells in human patients. Such damage or malfunction may occur in schizophrenia and other forms of psychosis. The only current treatments for such conditions are symptomatic and require drugs which act upon dopamine receptors or dopamine uptake sites, consistent with the view that the improper functioning of the dopaminergic neurons which innervate these receptor-bearing neuronal populations may be involved in the disease process.

SUMMARY OF THE INVENTION

In one aspect, the present invention provides novel truncated glial cell line-derived neurotrophic factor (GDNF) protein products. In one embodiment, truncated GDNF proteins are produced by recombinant genetic engineering techniques. In an alternative embodiment, the truncated GDNF proteins are synthesized by chemical techniques, or a combination of the recombinant and chemical techniques.

The truncated GDNF protein products of the present invention include the proteins represented by the amino acid sequence X-[$Cys^{41}$-$Cys^{133}$]-Y. The amino acid residue numbering scheme of FIG. 1 (SEQ ID NO:2) is used to facilitate comparison to the mature GDNF protein. [$Cys^{41}$-$Cys^{133}$] represents the amino acid sequence of $Cys^{41}$ through $Cys^{133}$ as depicted in FIG. 1 (SEQ ID NO:2). Y represents the carboxy terminal group of $Cys^{133}$ or a carboxy-terminus amino acid residue of $Ile^{134}$. X represents a methionylated or nonmethionylated amine group of $Cys^{41}$ or amino-terminus amino acid residue(s) selected from the group:

```
                                         G
                                        RG
                                       NRG
                                      KNRG   (SEQ ID NO:3)
                                     GKNRG   (SEQ ID NO:4)
                                    RGKNRG   (SEQ ID NO:5)
                                   QRGKNRG   (SEQ ID NO:6)
                                  GQRGKNRG   (SEQ ID NO:7)
                                 RGQRGKNRG   (SEQ ID NO:8)
                                RRGQRGKNRG   (SEQ ID NO:9)
                       G        RRGQRGKNRG   (SEQ ID NO:10)
                      KG        RRGQRGKNRG   (SEQ ID NO:11)
                     GKG        RRGQRGKNRG   (SEQ ID NO:12)
                    RGKG        RRGQRGKNRG   (SEQ ID NO:13)
                   SRGKG        RRGQRGKNRG   (SEQ ID NO:14)
                  NSRGKG        RRGQRGKNRG   (SEQ ID NO:15)
                 ENSRGKG        RRGQRGKNRG   (SEQ ID NO:16)
                PENSRGKG        RRGQRGKNRG   (SEQ ID NO:17)
               NPENSRGKG        RRGQRGKNRG   (SEQ ID NO:18)
              ANPENSRGKG        RRGQRGKNRG   (SEQ ID NO:19)
           A  ANPENSRGKG        RRGQRGKNRG   (SEQ ID NO:20)
          AA  ANPENSRGKG        RRGQRGKNRG   (SEQ ID NO:21)
         AAA  ANPENSRGKG        RRGQRGKNRG   (SEQ ID NO:22)
        QAAA  ANPENSRGKG        RRGQRGKNRG   (SEQ ID NO:23)
        RQAAA ANPENSRGKG        RRGQRGKNRG   (SEQ ID NO:24)
       NRQAAA ANPENSRGKG        RRGQRGKNRG   (SEQ ID NO:25)
       RNRQAAA ANPENSRGKG       RRGQRGKNRG   (SEQ ID NO:26)
      ERNRQAAA ANPENSRGKG       RRGQRGKNRG   (SEQ ID NO:27)
     RERNRQAAA ANPENSRGKG       RRGQRGKNRG   (SEQ ID NO:28)
    RRERNRQAAA ANPENSRGKG       RRGQRGKNRG   (SEQ ID NO:29)
  P RRERNRQAAA ANPENSRGKG       RRGQRGKNRG   (SEQ ID NO:30)
 LP RRERNRQAAA ANPENSRGKG       RRGQRGKNRG   (SEQ ID NO:31)
```

```
    VLP RRERNRQAAA ANPENSRGKG RRGQRGKNRG   (SEQ ID NO:32)

AVLP RRERNRQAAA ANPENSRGKG RRGQRGKNRG   (SEQ ID NO:33)

MAVLP RRERNRQAAA ANPENSRGKG RRGQRGKNRG   (SEQ ID NO:34)

QMAVLP RRERNRQAAA ANPENSRGKG RRGQRGKNRG   (SEQ ID NO:35)

KQMAVLP RRERNRQAAA ANPENSRGKG RRGQRGKNRG  (SEQ ID NO:36)

DKQMAVLP RRERNRQAAA ANPENSRGKG RRGQRGKNRG  (SEQ ID NO:37)

PDKQMAVLP RRERNRQAAA ANPENSRGKG RRGQRGKNRG (SEQ ID NO:38)
```

It is contemplated that such truncated GDNF protein products would include truncated GDNF protein having the amino acid sequence as represented by X-[$Cys^{41}$-$Cys^{133}$]-Y and variants and derivatives thereof. Thus, the truncated GDNF protein products of the present invention also include addition, substitution and internal deletion variants and derivatives of the amino acid sequences represented by X-[$Cys^{41}$-$Cys^{133}$]-Y. The truncated GDNF protein products further include methionylated or nonmethionylated forms as well as glycosylated or non-glycosylated forms of truncated GDNF protein.

Exemplary truncated GDNF proteins of the present invention include [$Arg^{16}$-$Ile^{134}$], [$Asn^{22}$-$Ile^{134}$], [$Pro^{23}$-$Ile^{134}$], [$Ser^{26}$-$Ile^{134}$], [$Arg^{32}$-$Ile^{134}$], [$Gly^{33}$-$Ile^{134}$], [$Lys^{37}$-$Ile^{134}$] and [$Asn^{38}$-$Ile^{134}$] truncated GDNF proteins, either methionylated or nonmethionylated, and variants and derivatives thereof. Presently preferred truncated GDNF proteins of the present invention include [$Lys^{37}$-$Ile^{134}$] and [$Asn^{38}$-$Ile^{134}$] truncated GDNF proteins, either methionylated or nonmethionylated, and variants and derivatives thereof. Exemplary substitution variants are the [$Asn^{22}\Delta Ser^{22}$-$Ile^{134}$] and [$Pro^{23}$-$Lys^{37}\Delta Asn^{37}$-$Ile^{134}$] truncated GDNF proteins. An exemplary addition variant is the Ser-[$Pro^{23}$-$Ile^{134}$] truncated GDNF protein.

In another aspect of the present invention, the truncated GDNF proteins may be made in glycosylated or non-glycosylated forms. Derivatives of truncated GDNF protein typically involve attaching the truncated GDNF protein to a water soluble polymer. For example, the truncated GDNF protein may be conjugated to one or more polyethylene glycol molecules to decrease the precipitation of the truncated GDNF protein product in an aqueous environment.

Yet another aspect of the present invention includes the various polynucleotides encoding truncated GDNF proteins. These nucleic acid sequences are generally used in the expression of truncated GDNF in a eukaryotic or prokaryotic host cell, wherein the expression product or a derivative thereof is characterized by the ability to increase dopamine uptake by dopaminergic cells. The polynucleotides may also be used in cell therapy or gene therapy applications. Suitable nucleic acid sequences include those specifically depicted in the Figures as well as additional degenerate sequences and naturally occurring allelic variations.

A further aspect of the present invention involves vectors containing the polynucleotides encoding truncated GDNF proteins operatively linked to amplification and/or expression control sequences. Both prokaryotic and eukaryotic host cells may be stably transformed or transfected with such vectors to express the truncated glial derived neurotrophic factor. The present invention further includes the recombinant production of a truncated GDNF protein wherein such transformed or transfected host cells are grown in a suitable nutrient medium, and the truncated GDNF expressed by the cells is, optionally, isolated from the host cells and/or the nutrient medium. The present invention further includes the use of polynucleotides encoding truncated GDNF and vectors containing such polynucleotides in gene therapy or cell therapy.

In another aspect, the present invention involves a recombinantly produced GDNF composition containing a mixture of a mature GDNF protein and one or more truncated GDNF proteins derived therefrom, wherein the mature GDNF protein has a molecular weight of approximately 44 kDa, and wherein the truncated GDNF protein has a molecular weight of approximately 36 to 40 kDa. The GDNF composition may contain at least two truncated GDNF species wherein a first species has a molecular weight of approximately 36 kDa and a second species has a molecular weight of approximately 40 kDa. The truncated GDNF species having a molecular weight of approximately 40 kDa is a heterodimer of a GDNF monomer having a molecular weight of approximately 22 kDa and a truncated GDNF monomer having a molecular weight of approximately 18 kDa. It is also contemplated that one or more of the truncated GDNF species may be isolated from such a mixture for therapeutic use.

Another aspect of the present invention includes pharmaceutical compositions containing truncated GDNF protein product. Typically, the truncated GDNF protein product is formulated in association with a pharmaceutically acceptable vehicle. A variety of other formulation materials may be used to facilitate manufacture, storage, handling, delivery and/or efficacy. In another aspect of the present invention, truncated GDNF protein products increase dopamine uptake and survival of dopaminergic neurons. Thus, the truncated GDNF protein products are particularly suitable for the treatment of damage to the nervous system caused by injury or disease, such as Parkinson's Disease.

Additional aspects and advantages of the invention will be apparent to those skilled in the art upon consideration of the following description, which details the practice of the present invention.

BRIEF DESCRIPTION OF THE FIGURES

Numerous features and advantages of the present invention will become apparent upon review of the figures, wherein:

FIG. 1 depicts a nucleic acid sequence (SEQ ID NO:1) encoding mature human glial cell line-derived neurotrophic factor (hGDNF). Also depicted is the amino acid sequence (SEQ ID NO:2) of the mature human GDNF protein.

FIG. 3 depicts a restriction map of an alternative nucleic acid sequence (SEQ ID NO:39) encoding GDNF and truncated GDNF polynucleotides.

FIG. 4 depicts a restriction map of yet another nucleic acid sequence (SEQ ID NO:40) encoding GDNF and truncated GDNF polynucleotides.

FIG. 5 depicts a nucleic acid sequence (SEQ ID NO:41) encoding [Pro$^{23}$-Lys$^{37}$ΔAsn$^{37}$-Ile$^{134}$] truncated GDNF protein substitution variant (SEQ ID NO:42). This protein may also be described as a Met-Ser-[Pro$^{23}$-Lys$^{37}$ΔAsn$^{37}$-Ile$^{134}$] truncated GDNF protein addition/substitution variant.

FIG. 6 depicts a nucleic acid sequence (SEQ ID NO:43) encoding an [Arg$^{32}$-Ile$^{134}$] truncated GDNF protein (SEQ ID NO:44).

FIG. 7 depicts a nucleic acid sequence (SEQ ID NO:45) encoding a [Gly$^{33}$-Ile$^{134}$] truncated GDNF protein (SEQ ID NO:46).

FIG. 8 depicts the amino acid sequence of mature hGDNF (SEQ ID NO:47) in comparison to several exemplary truncated GDNF proteins: Met-[Arg$^{32}$-Ile$^{134}$] (SEQ ID NO:48), Met-[Gly$^{33}$-Ile$^{134}$] (SEQ ID NO:49) and Met-Ser-[Pro$^{23}$-Lys$^{37}$ΔAsn$^{37}$-Ile$^{134}$] (SEQ ID NO:50).

DETAILED DESCRIPTION OF THE INVENTION

Figure 2:
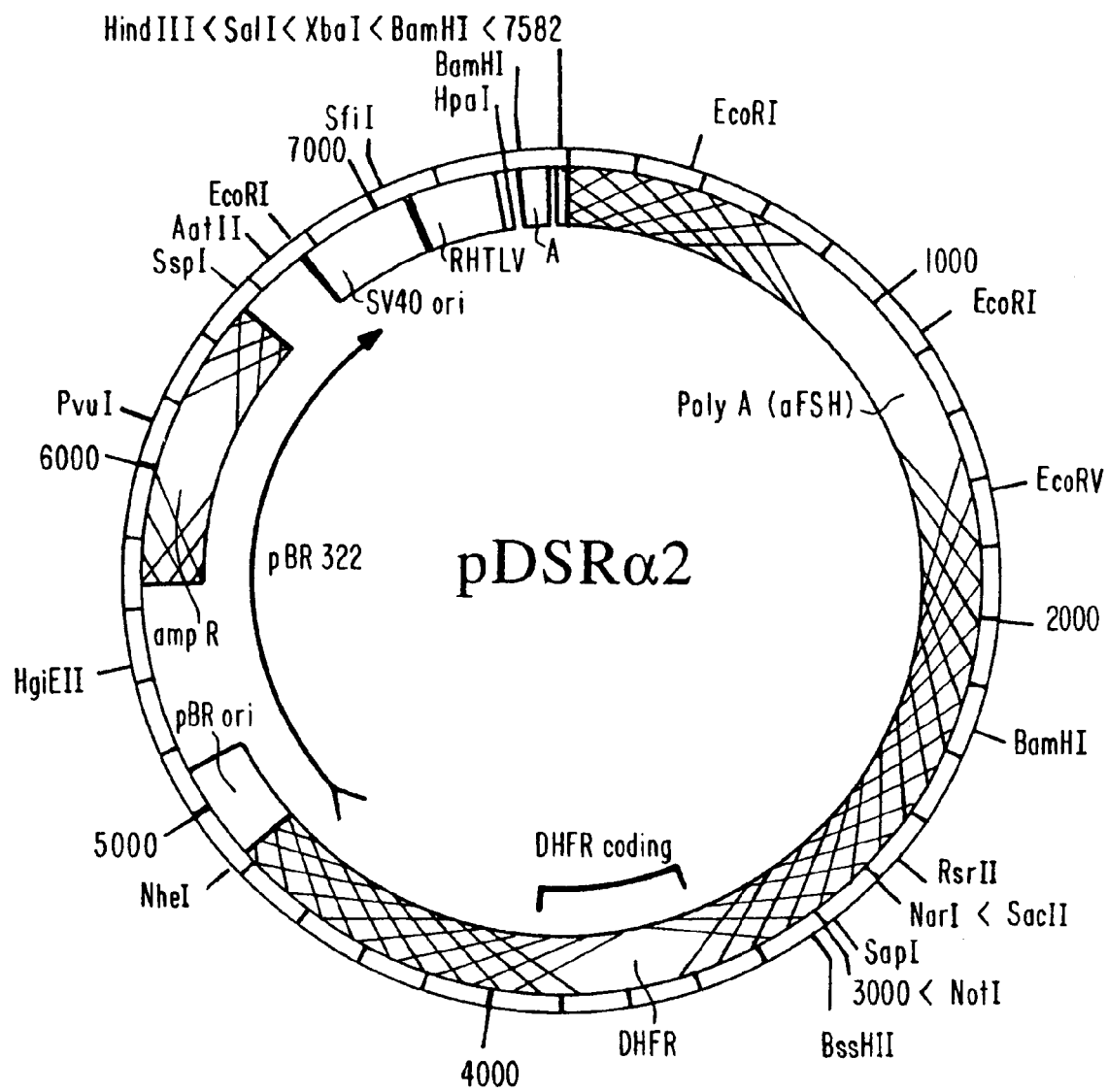
FIG. 2 depicts a diagram of a plasmid construction made for the expression of recombinant truncated GDNF proteins.

Human glial cell line-derived neurotrophic factor (hGDNF) is synthesized as a precursor that is processed and secreted as a mature protein of 134 amino acids. It was previously determined that mature human GDNF has the amino acid sequence depicted in FIG. 1 (SEQ ID NO:2).

The present invention is based on the unexpected discovery that the mature GDNF protein may be reduced in size (also referred to herein as a "clipped" or "truncated" protein or truncated GDNF protein) yet retain its biological activity. The clipped protein was first discovered during the recombinant production of GDNF in Chinese hamster ovary (CHO) cells. In brief, the recombinant human GDNF (rhGDNF) was prepared as follows. A nucleic acid sequence encoding the entire open reading frame of the mature human GDNF protein was cloned into an expression plasmid. The nucleic acid sequence was confirmed to be correct (by DNA sequencing as the equivalent of the hGDNF sequence in GeneBank) and was translated to an amino acid sequence identical to the published sequence for mature human GDNF (Lin et al., *Science* 260, 1130-1132, 1993). The plasmid DNA was linearized and transfected into dihydrofolate reductase-deficient CHO cells (CHOd⁻ cells) using the calcium phosphate precipitation method. Transfected cells were cultured in a selective medium, and those colonies that survived the selection process were chosen for individual analysis of hGDNF expression.

Serum-free conditioned media from the individual clones were collected and subjected to Western blot analysis using antisera specific for hGDNF. The antisera involved rabbit polyclonal antibodies elicited from rabbits immunized with recombinant hGDNF expressed in *Escherichia coli*. Under reducing conditions, the hGDNF that was present in these samples was resolved into two major bands having apparent molecular weights of approximately 22 kDa and 18 kDa. Each band consisted of a closely spaced doublet of approximately 22+22.5 kDa and 18+17.5 kDa, respectively (for simplicity, these doublets will be referred as the 22 kDa and 18 kDa bands or species).

GDNF had previously been reported to exist as a disulfide-bonded homodimer composed of two identical subunits of the mature GDNF protein having a molecular weight of approximately 20 to 22 kDa. When GDNF was analyzed under non-reducing conditions, it was reported that a broad band of 32 to 42 kDa (Lin et al., *Science* 260, 1130-1132, 1993) or 33 to 45 kDa (Lin et al., *J. Neurochem.* 63(2), 758-768, 1994) had been identified. The existence of the range was interpreted as being due to the heterogeneity of glycosylation on the mature monomers and was further substantiated with de-glycosylation experiments.

While the present 22 kDa band corresponds to the mature GDNF protein reported in the literature, the 18 kDa band has not previously been reported. The relative amounts of the 22 kDa and the 18 kDa protein varied in samples collected from individual clones. In addition, it was found that multiple harvests from the same clone showed a variable ratio of the two bands. Moreover, it was found that storage of the CHO-expressed GDNF protein frequently led to an increase in the presence of the 18 kDa band with a concurrent decrease of the 22 kDa band.

When conditioned medium from the transformed CHOd⁻ cells was analyzed under nonreducing conditions by Western blots, three well-resolved bands with apparent molecular weights of 36, 40 and 44 kDa were observed. This finding was also in contrast to previous reports. The relative intensity of these bands was variable, but they correlated well with the ratio of the 22 and 18 kDa monomer bands present in each of the samples. Upon further analysis with monoclonal antisera, it was determined that the three bands in the nonreducing gel corresponded to three possible dimers composed of the two monomers. The largest 44 kDa protein is a dimer of two 22 kDa mature GDNF proteins as previously reported. The intermediate 40 kDa protein consists of a dimer in which one mature protein has been reduced in molecular weight to an 18 kDa form. The smallest 36 kDa dimer appears to contain two 18 kDa proteins, i.e., both 22 kDa forms have been reduced in molecular weight. This data demonstrated for the first time not only the presence of a novel form of GDNF monomer but also the presence of the clipped GDNF protein in the dimeric configuration. It was also found that, when stored, the monomer composition of the samples shifted towards that of the clipped form and the corresponding dimer species, i.e., the amount of the 36 kDa protein was seen to increase.

Studies were then performed to identify which part of the protein was being eliminated or changed to cause of the reduction in molecular weight in comparison to that of the previously reported mature GDNF protein. It was first determined that the reduction in molecular weight was not due to changes in glycosylation.

GDNF contains two potential N-linked glycosylation sites and has been reported to be glycosylated. The clipped protein, however, is not simply the nonglycosylated or underglycosylated form of mature GDNF. This was demonstrated in deglycosylation experiments wherein samples were treated with N-glycanase, O-glycanase and neuraminidase. On reducing gels, the 18 kDa protein was reduced to a 13.5 kDa band by N-glycanase digestion indicating the presence of an equivalency of 4.5 kDa of N-linked sugar. Treatment with neuraminidase and O-glycanase caused the 18 kDa band to shift slightly to 17 kDa. This indicated the presence of O-linked sugars on the protein. The mature 22 kDa band has been reported to be glycosylated and was also reduced to 18 kDa (i.e., also by 4.5 kDa) by N-glycanase. This was further confirmed through the use of a monoclonal antibody which is specific for the 22 kDa band on the gel. The glycanase digestion pattern of the nonreduced dimer was more complicated, but was interpretable and consistent with the initial assignment of the three forms.

As a result, the 4.5 kDa reduction in molecular weight of the protein was then viewed as resulting from the deletion of approximately 30-35 amino acid residues rather than from changes in glycosylation. The deletion was expected to most likely occur at the amino-terminus of the mature GDNF protein for the following reasons. Mature GDNF contains a total of seven cystines. If the deletion were from the carboxyl terminus, 2 to 4 of the seven cystines would be lost, and this would likely result in an inactive protein. However, when a test sample consisting of predominantly the clipped form was subjected to a bioassay to measure its dopaminergic neuron neurotrophic activity, the sample demonstrated comparable activity to a sample which contained proportionally more of the mature form of GDNF.

The site of cleavage was then determined via amino acid sequence analysis of the purified protein. Samples were sequenced, according to manufactur's instructions, using an Applied Biosystems 494A protein sequencer for ten cycles. While amino acid sequence analysis techniques and procedures are well known to those skilled in the art, further descriptions of the sequencing of proteins are provided in Fausset et al., *Electrophoresis* 12:22-27, 1991 and European Patent Application No. 90310899, granted Jul. 12, 2000, EP Patent No. 0423980, entitled "Stem Cell Factor", the disclosures of which are hereby incorporated by reference. Upon analysis, it was determined that the amino terminus of the clipped protein was "RGQRGK" or Arg-Gly-Gln-Arg-Gly-Lys. Therefore, the first 31 amino acids had been removed from the mature protein in the conditioned media. The remaining amino acid sequence of the clipped protein, beginning with amino acid Arg$^{32}$, was otherwise consistent with that of the mature GDNF amino acid sequence depicted in FIG. 1 (SEQ ID NO:2).

The [Arg$^{32}$-Ile$^{134}$] truncated GDNF protein was found to be active, on a qualitative basis, in a dopaminergic neuron assay. The dopaminergic neurotrophic activity assay is used to identify neurotrophic factors that may be beneficial in treating Parkinson's disease. The assay is based on a previously described assay (Friedman et al., *Neuro. Sci. Lett.* 79:65-72, 1987, the disclosure of which is hereby incorporated by reference) and may include modifications as described in Lin et al. (see U.S. patent application Ser. No. 08/182,183 filed May 23, 1994 and its parent applications; PCT/US92/07888 filed Sep. 17, 1992 (WO 93/06116); and European Patent Application No. 92921022.7 (Publication No. EP 610 254)). A detailed description of the assay is provided in Example 5, below.

A subsequent purification procedure, followed by amino acid sequencing, led to the discovery of another protein from which the first 36 amino acid residues had been removed from the N-terminus of mature GDNF: a [Lys$^{37}$-Ile$^{134}$] truncated GDNF protein, with an N-terminal sequence of KNRG(C)VL-. Again, the remaining amino acid residues of the clipped protein were otherwise consistent with those of the mature human GDNF amino acid sequence. The [Lys$^{37}$-Ile$^{134}$] truncated GDNF protein was also analyzed in the dopamine uptake bioassay. This truncated GDNF protein was found to be active with an ED50 of about 50 pg/ml, similar to that of purified recombinant *E. coli*-expressed, mature GDNF.

It was further discovered that bacterially expressed mature GDNF could be changed to a truncated form. Mature GDNF, expressed in transformed *E. coli* (as described in Lin et al., U.S. patent application Ser. No. 08/182,183, supra), was incubated with CHO-derived conditioned media. Recombinant *E. coli* GDNF has an apparent molecular weight of 17 kDa on reducing gel. When the material was mixed with CHO cell conditioned media and incubated for five days at 4° C., the protein was clipped completely to 12.5 kDa. This cleavage was less complete with one hour or 24 hours of incubation, suggesting a time-dependent process under such conditions. It was also found that simply incubating recombinant *E. coli* GDNF overnight with media containing 0.1% fetal bovine serum did not generate the clipped form. Thus, the presence of live cells in the culture seems to be necessary for the clipping process to occur. It is possible, therefore, that the clipping event may also occur in vivo within certain tissues.

In addition, it was found that derivatives of mature *E. coli*-expressed hGDNF, such as pegylated GDNF (also described in Lin et al., U.S. patent application Ser. No. 08/182,183, supra) may be processed to a truncated form in the presence of CHO-derived conditioned media. Mature GDNF may be pegylated at the amino terminus in order to enhance its clearance time in circulation. Pegylation increases the size of the protein, and the modified mature GDNF migrates at about 45 kDa under reduced conditions. As with the non-pegylated mature form, the incubation of pegylated *E. coli* GDNF with CHO cell (untransfected) conditioned media generated a 12.5 kDa band. In both cases, the 12.5 kDa species was present as a disulfide-bonded dimer as shown on non-reducing gels. The generation of this clipped form from the N-terminally pegylated mature protein further demonstrated that the clipping event occurred at the N-terminus of the protein since the pegylated residue was lost during the clipping process.

Based on the these findings and because the clipping event may also occur in vivo, a truncated form of the GDNF protein may be the ultimate naturally processed form of hGDNF under physiological conditions. Therefore, it was considered advantageous to produce a truncated GDNF protein, or derivative thereof, for therapeutic use. For example, a directly expressed or synthesized truncated GDNF protein, such as the [Arg$^{32}$-Ile$^{134}$] truncated GDNF protein, would be expected to be resistant to the above-described proteolytic activity. Moreover, if it was desired to produce a truncated GDNF derivative, such as a pegylated [Arg$^{32}$-Ile$^{134}$] truncated GDNF protein, the resulting derivative would be expected to have the advantage of not being susceptible to the specific clipping which was observed with the mature GDNF derivative.

Additional advantages can also be expected of truncated GDNF protein products. First, the pI of a truncated protein, such as the [Arg$^{32}$-Ile$^{134}$] truncated GDNF protein, will be reduced from about 10 to about 8.0-8.5. This makes the protein significantly less basic which could in turn provide beneficial effects including better receptor binding and decreased cytotoxicity at the site of administration, such as an intrathecal injection site. Second, within the first 26 amino acids of the mature GDNF amino acid sequence are two deamidation sites: Arg-Asn-Arg (amino acids 14-16) and Glu-Asn-Ser (amino acids 24-26). The absence of one or both of these sites in a truncated GDNF protein is expected to increase the stability of the protein.

Truncated GDNF Protein Products

In a basic embodiment, the truncated GDNF proteins of the present invention may be represented by the following amino acid sequence wherein the amino acid residue numbering scheme of FIG. 1 is used to facilitate comparison to the mature GDNF protein:

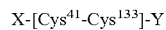

wherein

[Cys$^{41}$-Cys$^{133}$] represents the amino acid sequence of Cys$^{41}$ through Cys$^{133}$ as depicted in FIG. 1 (SEQ ID NO:2);

Y represents the carboxy terminal group of Cys$^{133}$ or a carboxy-terminus amino acid residue of Ile$^{134}$; and X represents a methionylated or nonmethionylated amine group of Cys$^{41}$ or amino-terminus amino acid residue(s) selected from the group:

```
                                  G
                                 RG
                                NRG
                               KNRG  (SEQ ID NO:3)
                              GKNRG  (SEQ ID NO:4)
                             RGKNRG  (SEQ ID NO:5)
                            QRGKNRG  (SEQ ID NO:6)
                           GQRGKNRG  (SEQ ID NO:7)
                          RGQRGKNRG  (SEQ ID NO:8)
                         RRGQRGKNRG  (SEQ ID NO:9)
                       G RRGQRGKNRG  (SEQ ID NO:10)
                      KG RRGQRGKNRG  (SEQ ID NO:11)
                     GKG RRGQRGKNRG  (SEQ ID NO:12)
                    RGKG RRGQRGKNRG  (SEQ ID NO:13)
                   SRGKG RRGQRGKNRG  (SEQ ID NO:14)
                  NSRGKG RRGQRGKNRG  (SEQ ID NO:15)
                 ENSRGKG RRGQRGKNRG  (SEQ ID NO:16)
                PENSRGKG RRGQRGKNRG  (SEQ ID NO:17)
               NPENSRGKG RRGQRGKNRG  (SEQ ID NO:18)
              ANPENSRGKG RRGQRGKNRG  (SEQ ID NO:19)
            A ANPENSRGKG RRGQRGKNRG  (SEQ ID NO:20)
           AA ANPENSRGKG RRGQRGKNRG  (SEQ ID NO:21)
          AAA ANPENSRGKG RRGQRGKNRG  (SEQ ID NO:22)
         QAAA ANPENSRGKG RRGQRGKNRG  (SEQ ID NO:23)
        RQAAA ANPENSRGKG RRGQRGKNRG  (SEQ ID NO:24)
       NRQAAA ANPENSRGKG RRGQRGKNRG  (SEQ ID NO:25)
      RNRQAAA ANPENSRGKG RRGQRGKNRG  (SEQ ID NO:26)
     ERNRQAAA ANPENSRGKG RRGQRGKNRG  (SEQ ID NO:27)
    RERNRQAAA ANPENSRGKG RRGQRGKNRG  (SEQ ID NO:28)
   RRERNRQAAA ANPENSRGKG RRGQRGKNRG  (SEQ ID NO:29)
 P RRERNRQAAA ANPENSRGKG RRGQRGKNRG  (SEQ ID NO:30)
LP RRERNRQAAA ANPENSRGKG RRGQRGKNRG  (SEQ ID NO:31)
VLP RRERNRQAAA ANPENSRGKG RRGQRGKNRG  (SEQ ID NO:32)
AVLP RRERNRQAAA ANPENSRGKG RRGQRGKNRG  (SEQ ID NO:33)
MAVLP RRERNRQAAA ANPENSRGKG RRGQRGKNRG  (SEQ ID NO:34)
QMAVLP RRERNRQAAA ANPENSRGKG RRGQRGKNRG  (SEQ ID NO:35)
KQMAVLP RRERNRQAAA ANPENSRGKG RRGQRGKNRG  (SEQ ID NO:36)
DKQMAVLP RRERNRQAAA ANPENSRGKG RRGQRGKNRG  (SEQ ID NO:37)
PDKQMAVLP RRERNRQAAA ANPENSRGKG RRGQRGKNRG  (SEQ ID NO:38)
```

As used herein, the term "truncated GDNF protein product" includes biologically active synthetic or recombinant truncated GDNF proteins, truncated GDNF proteins produced from mature GDNF, biologically active truncated GDNF variants (including insertion, substitution and deletion variants), and chemically modified derivatives thereof. Also included are truncated GDNF proteins that are substantially homologous to the human GDNF protein having the amino acid sequence set forth in SEQ ID NO:2.

The term "biologically active" as used herein means that the truncated GDNF protein demonstrates similar neurotrophic properties, but not necessarily all of the same properties, and not necessarily to the same degree, as the GDNF protein having the amino acid sequence set forth in SEQ ID NO:2. The selection of the particular neurotrophic properties of interest depends upon the use for which the truncated GDNF protein product is being administered. The truncated GDNF protein products are biologically active and demonstrate dopaminergic neuron survival characteristics similar to that demonstrated by mature GDNF protein using the evaluation of dopamine uptake and tyrosine hydroxylase (TH) expression as an exemplary bioassay, as discussed in the examples, below.

The term "substantially homologous", as used herein, means a degree of homology to the human GDNF having the amino acid sequence set forth in SEQ ID NO:2 that is preferably in excess of 70%, most preferably in excess of 80%, and even more preferably in excess of 90% or even 95%. The percentage of homology as described herein is calculated as the percentage of amino acid residues found in the smaller of the two sequences which align with identical amino acid residues in the sequence being compared when four gaps in a length of 100 amino acids may be introduced to assist in that alignment as set forth by Dayhoff, in *Atlas of Protein Sequence and Structure* Vol. 5, p. 124 (1972), National Biochemical Research Foundation, Washington, D.C., the disclosure of which is hereby incorporated by reference. Also included as substantially homologous is any truncated GDNF protein which may be isolated by virtue of cross-reactivity with antibodies to the GDNF of SEQ ID NO:2 or whose genes may be isolated through hybridization with the gene or with segments of the gene encoding the GDNF of SEQ ID NO:1.

As will be apparent to those skilled in the art upon reading the present description, substantially homologous proteins will involve one or more deletions from, or additions or substitutions to, the amino acid residues of the truncated GDNF protein represented by X-[$Cys^{41}$-$Cys^{133}$]-Y. The production of such variants is described in further detail below. It will be further appreciated that because the present invention clearly addresses "truncated" GDNF proteins, the amino-terminus addition variants are contemplated as including the addition of a methionine residue, or non-GDNF amino acid residue or sequence, but do not include the addition of an amino acid residue(s) that would result in the reconstruction of the mature GDNF protein. Truncated GDNF proteins based upon naturally occurring allelic mutants or variants are also within the scope of the present invention. The production of variant truncated GDNF protein is described in further detail below.

Lin et al. (U.S. patent application Ser. No. 08/182,183, supra) described the truncation of mature GDNF at the carboxyl terminus by proteolytic processing of the Lys-Arg residues which are the sixth and fifth residues, respectively, from the carboxyl terminal end of mature GDNF (i.e., $Lys^{129}$-$Arg^{130}$ according to the amino acid residue numbering of FIG. 1 (also as in SEQ ID NO:1 or SEQ ID NO:2). Such a truncation would eliminate two cysteine residues from the mature GDNF protein. This would be likely to result in improper folding of the protein, and therefore, would result in the formation of an inactive protein. In contrast, the X-[$Cys^{41}$-$Cys^{133}$]-Y truncated GDNF protein products of the present invention retain the $Cys^{131}$ and $Cys^{133}$ residues and are active proteins as determined by dopamine uptake assay.

In one embodiment of the present invention, preferred truncated GDNF protein products lack one or more deamidation sites. Such a lack of deamidation sites would result in the enhanced biochemical stability of the purified protein and a decrease in possible degradation products, thereby resulting in a more storage stable protein. An exemplary truncated GDNF protein product is the [$Ser^{26}$-$Ile^{134}$] truncated GDNF protein which lacks the sites which otherwise may lead to deamidation of the mature protein. Alternatively, the [$Arg^{16}$-$Ile^{134}$] truncated GDNF protein would lack at least the first deamidation site otherwise present in the mature protein.

A currently preferred truncated GDNF protein product is [$Arg^{32}$-$Ile^{134}$] truncated GDNF protein. This truncated GDNF protein lacks the site at or near which proteolytic clipping of the mature protein occurs. Therefore, this truncated GDNF protein is expected to be resistant to the processing event which may also occur in vivo. Another currently preferred truncated GDNF protein product is the [$Lys^{37}$-$Ile^{134}$] truncated GDNF protein. This truncation would further reduce the pI of the truncated protein, as would other truncations in which residues up to and including $Gly^{40}$ and $Ile^{134}$ are removed from the N- and C-terminals, respectively. The presently most preferred truncated GDNF protein products retain all of the cysteine residues found in mature GDNF protein, but lack any discernible sites for rapid proteolytic processing of the truncated GDNF protein during expression and manufacturing or following in vivo administration. These preferred proteins include the [$Arg^{32}$-$Ile^{134}$], [$Gly^{33}$-$Ile^{134}$], [$Gln^{34}$-$Ile^{134}$], [$Arg^{35}$-$Ile^{134}$], [$Gly^{36}$-$Ile^{134}$], [$Lys^{37}$-$Ile^{134}$], [$Asn^{38}$-$Ile^{134}$] and [$Arg^{39}$-$Ile^{134}$] truncated GDNF protein products.

Similar to the results previously described for mature GDNF by Lin et al. (U.S. patent application Ser. No. 07/855,413, now abandoned), the truncated GDNF proteins of the present invention have demonstrated the ability to increase dopamine uptake by the embryonic precursors of the *substantia nigra* dopaminergic neurons. Bioassays of the truncated GDNF proteins are further described in Example 4, below.

The novel truncated GDNF proteins are typically isolated and purified to form truncated GDNF proteins which are substantially free from the presence of other (non-GDNF) proteinaceous materials. Preferably, the truncated GDNF protein products are about 80% free of other proteins which may be present due to the production technique used in the manufacture of the truncated GDNF protein product. More preferably, the truncated GDNF protein products are about 90% free of other proteins, particularly preferably, about 95% free of other proteins, and most preferably about >98% free of other proteins. In addition, the present invention furnishes the unique advantage of providing polynucleotide sequences for the manufacture of homogeneous truncated GDNF proteins. For example, the use of the polynucleotide sequence encoding the [$Arg^{32}$-$Ile^{134}$] truncated GDNF protein allows the recombinant production of the truncated GDNF protein in *E. coli* and other appropriate expression systems. In other words, the novel polynucleotides allow the production of truncated GDNF proteins which are not susceptible to proteolytic processing, or which have reduced susceptibility to such processing or other biochemical processing effects as described above. Thus, the novel polynucleotides make it easier to prepare and/or isolate single species truncated GDNF proteins, and therefore, the truncated GDNF proteins and/or products thereof do not contain or contain decreased amounts of the above-described mixture of hetero- and homodimers. It will be appreciated, however, that the final truncated GDNF protein products may be combined with other factors, chemical compositions and/or suitable pharmaceutical formulation materials prior to administration, as described in further detail below.

In one aspect of the present invention, the truncated GDNF proteins are advantageously produced via recombinant techniques because they are capable of achieving comparatively higher amounts of protein at greater purity. Recombinant truncated GDNF protein forms include glycosylated and non-glycosylated forms of the protein, and protein expressed in bacterial, mammalian or insect cell systems. Alternatively, the truncated GDNF proteins may be chemically synthesized. Currently preferred production methods are described in greater detail below.

Truncated GDNF Variants and Derivatives

A. Truncated GDNF Variants

Another aspect of the present invention includes variants of truncated GDNF protein. The term "truncated GDNF protein products" as used herein includes variant proteins in which amino acids have been deleted from ("deletion variants"), inserted into ("addition variants"), or substituted for ("substitution variants"), residues within the amino acid sequence of naturally-occurring GDNF. Such variants are prepared by introducing appropriate nucleotide changes into the DNA encoding the protein or by in vitro chemical synthesis of the desired protein. It will be appreciated by those skilled in the art that many combinations of deletions, insertions, and substitutions can be made provided that the final protein possesses GDNF biological activity.

Mutagenesis techniques for the replacement, insertion or deletion of one or more selected amino acid residues are well known to one skilled in the art (e.g., U.S. Pat. No. 4,518,584, the disclosure of which is hereby incorporated by reference.) There are two principal variables in the construction of amino acid sequence variants: the location of the mutation site and the nature of the mutation. In designing truncated GDNF variants, the location of the mutation site and the nature of the mutation will depend on the biochemical characteristic(s) to be modified. The mutation sites can be modified individually or in series, e.g., by (1) substituting first with conservative amino acid choices and then with more radical selections depending upon the results achieved, (2) deleting the target amino acid residue, or (3) inserting amino acid residues adjacent to the located site.

Amino acid sequence deletions generally range from about 1 to 30 amino acid residues, more usually from about 1 to 10 residues, and typically from about 1 to 5 residues. For example, deletions in the "X" portion of the amino acid residues located N-terminally to $Cys^{41}$ may range from approximately 1 to 30 residues, while deletions between the cysteine residues of $[Cys^{41}\text{-}Cys^{133}]$ are typically from about 1 to 5 residues, depending on the location, so as not to disrupt protein folding. Deletions within the truncated GDNF proteins may be made in regions of low homology with transforming growth factor-beta (TGF-β) family members. Deletions from truncated GDNF proteins in areas of substantial homology with other TGF-β family sequences will be more likely to modify the biological activity more significantly. The number of total deletions and/or consecutive deletions will be selected so as to preserve the tertiary structure of truncated GDNF protein in the affected domain, e.g., cysteine crosslinking.

Amino acid sequence additions may include amino- and/or carboxyl-terminal fusions ranging in length from one residue to one hundred or more residues, as well as internal intrasequence insertions of single or multiple amino acid residues. Internal additions may range generally from about 1 to 10 amino acid residues, more typically from about 1 to 5 amino acid residues, and usually from about 1 to 3 amino acid residues. As described above, the amino-terminus addition variants of the present invention are contemplated as including the addition of a methionine (for example, as an artifact of the direct expression of GDNF in bacterial recombinant cell culture) or a non-GDNF amino acid residue or sequence. Amino-terminus addition variants do not involve the addition of an amino acid residue(s) that would result in the reconstruction of the mature GDNF protein. A further example of a terminal insertion includes the fusion of a heterologous N-terminal signal sequence to the N-terminus to facilitate the secretion of protein from recombinant host cells. Such signal sequences generally will be obtained from, and thus be homologous to, the intended host cell species. Insertions or additions may also include amino acid sequences derived from the sequence of other neurotrophic factors.

Another group of variants are amino acid substitution variants. These variants have at least one amino acid residue in the truncated GDNF protein removed and a different residue inserted in its place. See, for example, FIG. 5 wherein naturally occurring $Asn^{22}$ was changed to Ser to facilitate further removal of the Met residue. Using the $X\text{-}[Cys^{41}\text{-}Cys^{133}]\text{-}Y$ amino acid sequence representation and the present definition of truncated GDNF protein products, such a truncated GDNF protein may be referred to either as a substitution variant Met-$[Asn^{22}\Delta Ser^{22}\text{-}Ile^{134}]$ truncated GDNF protein or an addition variant Met-Ser-$[Pro^{23}\text{-}Ile^{134}]$ truncated GDNF protein. Substitution variants include allelic variants, which are characterized by naturally-occurring nucleotide sequence changes in the species population that may or may not result in an amino acid change.

Specific mutations of the sequences of the truncated GDNF proteins may involve modifications of a glycosylation site (e.g., serine, threonine, or asparagine). The absence of glycosylation or only partial glycosylation may result from amino acid substitution or deletion at any asparagine-linked glycosylation recognition site or at any site of the protein that is modified by the addition of an O-linked carbohydrate. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro. A variety of amino acid substitutions or deletions at one or both of the first or third amino acid positions of a glycosylation recognition site (and/or amino acid deletion at the second position) result in non-glycosylation at the modified tripeptide sequence. Thus, the expression of appropriately altered nucleotide sequences produces variants which are not glycosylated at that site. Alternatively, the sequence may be modified to add glycosylation sites to the truncated GDNF protein.

One method for identifying truncated GDNF amino acid residues or regions for mutagenesis is called "alanine scanning mutagenesis" as described by Cunningham and Wells (Science, 244:1081-1085, 1989). In this method, an amino acid residue or group of target residues are identified (e.g., charged residues such as Arg, Asp, His, Lys, and Glu) and replaced by a neutral or negatively charged amino acid (most preferably alanine or polyalanine) to effect the interaction of the amino acids with the surrounding aqueous environment in or outside the cell. Those domains demonstrating functional sensitivity to the substitutions then are refined by introducing additional or alternate residues at the sites of substitution.

Thus, the site for introducing an amino acid sequence modification is predetermined, and to optimize the performance of a mutation at a given site, alanine scanning or random mutagenesis may be conducted and the variants are screened for the optimal combination of desired activity and degree of activity.

The sites of greatest interest for substitutional mutagenesis include sites where the amino acids found in GDNF proteins from various species are substantially different in terms of side-chain bulk, charge, and/or hydrophobicity. Other sites of interest include those in which particular residues of GDNF-like proteins, obtained from various species, are identical. Such positions are generally important for the biological activity of a protein. Initially, these sites are modified by substitution in a relatively conservative manner. Such conservative substitutions are shown in Table 1 under the heading of preferred substitutions. If such substitutions result in a change in biological activity, then more substantial changes (exemplary substitutions) are introduced and/or other additions/deletions may be made, and the resulting products screened.

TABLE 1

Amino Acid Substitutions

| Original Residue | Preferred Substitutions | Exemplary Substitutions |
| --- | --- | --- |
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

Conservative modifications to the amino acid sequence (and the corresponding modifications to the encoding nucleic acid sequences) are expected to produce truncated GDNF proteins having functional and chemical characteristics similar to those of the truncated GDNF proteins described in the Examples, below. In contrast, substantial modifications in the functional and/or chemical characteristics of truncated GDNF proteins may be accomplished by selecting substitutions that differ significantly in their effect on maintaining (a) the structure of the polypeptide backbone in the area of the substitution, for example, as a sheet or helical conformation, (b) the charge or hydrophobicity of the protein at the target site, or (c) the bulk of the side chain. Naturally occurring residues are divided into groups based on common side chain properties:
 1) hydrophobic: norleucine, Met, Ala, Val, Leu, Iie;
 2) neutral hydrophilic: Cys, Ser, Thr;
 3) acidic: Asp, Glu;
 4) basic: Asn, Gln, His, Lys, Arg;
 5) residues that influence chain orientation: Gly, Pro; and
 6) aromatic: Trp, Tyr, Phe.

Non-conservative substitutions may involve the exchange of a member of one of these classes for another. Such substituted residues may be introduced into regions of the truncated GDNF proteins that are homologous with other TGF-β proteins, or into the non-homologous regions of the protein.

B. Truncated GDNF Derivatives

Chemically modified derivatives of truncated GDNF or truncated GDNF variants may be prepared by one skilled in the art given the disclosures herein. The chemical moieties most suitable for derivatization of truncated GDNF proteins include water soluble polymers. A water soluble polymer is desirable because the protein to which it is attached does not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations. The effectiveness of the derivatization may be ascertained by administering the derivative, in the desired form (i.e., by osmotic pump, or, more preferably, by injection or infusion, or further formulated for oral, pulmonary or other delivery routes), and determining its effectiveness.

Suitable water soluble polymers include, but are not limited to, polyethylene glycol (PEG), copolymers of ethylene glycol/propylene glycol, monomethoxy-polyethylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl pyrrolidone)polyethylene glycol, propropylene glycol homopolymers, prolypropylene oxide/ethylene oxide co-polymers, polyoxyethylated polyols (e.g., glycerol), polyethylene glycol propionaldehyde, and mixtures thereof. As used herein, polyethylene glycol is meant to encompass any of the forms of PEG that have been used to derivatize other proteins, such as mono-(C1-C10) alkoxy- or aryloxy-polyethylene glycol. Polyethylene glycol propionaldehyde may have advantages in manufacturing due to its stability in water. The polymer may be of any molecular weight, and may be branched or unbranched.

The present invention particularly relates to truncated GDNF protein products involving truncated GDNF protein linked to at least one PEG molecule. In another aspect, the present invention relates to truncated GDNF protein attached to at least one PEG molecule via an acyl or alkyl linkage.

Pegylation may be carried out by any of the pegylation reactions known in the art. See, for example: *Focus on Growth Factors* 3 (2): 4-10 (1992); EP 0 154 316; EP 0 401 384; and Malik et al., *Exp. Hematol.* 20: 1028-1035 (1992) (reporting pegylation of GM-CSF using tresyl chloride). Preferably, the pegylation is carried out via an acylation reaction or an alkylation reaction with a reactive water soluble polymer. These preferred means for derivatization are discussed in greater detail, below. For the acylation reactions, the polymer(s) selected preferably have a single reactive ester group. For the reductive alkylation reactions, the polymer(s) selected preferably have a single reactive aldehyde group. In addition, the selected polymer may be modified to have a single reactive group, such as an active ester for acylation or an aldehyde for alkylation, so that the degree of polymerization may be controlled. Generally, the water soluble polymer will not be selected from naturally-occurring glycosyl residues since these are usually made more conveniently by mammalian recombinant expression systems.

Acylation

In the present invention, pegylation by acylation generally involves reacting an active ester derivative of polyethylene glycol with a truncated GDNF protein. Any known or subsequently discovered reactive PEG molecule may be used to carry out the pegylation process. A preferred activated PEG ester is PEG esterified to N-hydroxysuccinimide ("NHS"). As used herein, "acylation" is contemplated to included without limitation the following types of linkages between a truncated GDNF protein and a water soluble polymer such as PEG: amide, carbamate, urethane, and the like. See *Bioconjugate Chem.* 5:133-140 (1994). Reaction conditions may be selected from any of those known in the pegylation art or those subsequently developed, but should avoid or limit exposure to reaction conditions such as temperatures, solvents, and pH levels that would inactivate the truncated GDNF protein to be modified.

Pegylation by acylation will generally result in a poly-pegylated truncated GDNF protein, wherein the lysine ε-amino groups are pegylated via an acyl linking group. Preferably, the connecting linkage will be an amide. Also preferably, the resulting product will be substantially only (e.g., ≧95%) mono-, di- or tri-pegylated. However, some conjugates with higher degrees of pegylation may be formed in amounts depending on the specific reaction conditions used. If desired, more purified pegylated conjugates may be prepared from the mixture by standard purification techniques, including, among others, dialysis, salting-out, ultrafiltration, ion-exchange chromatography, gel filtration chromatography and electrophoresis.

Alkylation

In the present invention, pegylation by alkylation generally involves reacting a terminal aldehyde derivative of PEG with a truncated GDNF protein in the presence of a reducing agent. Pegylation by alkylation can also result in a poly-pegylated truncated GDNF protein. In addition, one can manipulate the reaction conditions to favor pegylation substantially only at the α amino group of the N-terminus of the protein (i.e., a mono-pegylated species). In either case of mono-pegylation or polypegylation, the PEG groups are preferably attached to the protein via a —$CH_2$—NH— group. With particular reference to the —$CH_2$— group, this type of linkage is referred to herein as an "alkyl" linkage.

Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group-containing polymer is achieved. For example, one may selectively N-terminally pegylate the protein by performing the reaction at a pH which allows one to take advantage of the $pK_a$ differences between the ε-amino group of the lysine residues and that of the α-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer preferably has a single reactive aldehyde for coupling to the protein. Polyethylene glycol propionaldehyde, containing a single reactive aldehyde, may be used.

The present invention includes pegylated truncated GDNF proteins, wherein the PEG group(s) is (are) attached via acyl or alkyl groups. As discussed above, such truncated GDNF protein products may be mono-pegylated or poly-pegylated (e.g., containing 2-6, preferably 2-5, PEG groups). The PEG groups are generally attached to the protein at the α- or ε-amino groups of amino acids, but it is also contemplated that the PEG groups could be attached to any reactive group of to the protein, which is sufficiently reactive to become attached to a PEG group under suitable reaction conditions. Thus, polyethylene glycol may be covalently bound to a protein via a reactive group, such as, a free amino or carboxyl group. Reactive groups are those to which an activated PEG molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydryl groups may also be used as a reactive group for attaching PEG molecule(s). For therapeutic purposes, attachment at an amino group, such as attachment at the N-terminus or lysine group is typically preferred. Attachment at residues important for receptor binding should be avoided if receptor binding is desired.

In one aspect, the present invention provides for a substantially homogeneous preparation of mono-polymer/truncated GDNF protein conjugate wherein a polymer molecule has been attached substantially only (i.e., ≧95%) in a single location. More specifically, if PEG is used, the present invention also provides for pegylated a truncated GDNF protein lacking possibly antigenic linking groups, and having the PEG molecule directly coupled to the truncated GDNF protein.

In addition, derivatives may be prepared using glycosylated, non-glycosylated or de-glycosylated truncated GDNF proteins. Typically, non-glycosylated truncated GDNF proteins are used. For example, the prokaryote-expressed [$Arg^{32}$-$Ile^{134}$] truncated GDNF protein may be chemically derivatized to include mono- or poly-, e.g., 2-4, PEG moieties, attached via an acyl or alkyl group):

In general, chemical derivatization may be performed under any suitable condition used to react a biologically active substance with an activated polymer molecule. Methods for preparing pegylated truncated GDNF proteins will generally comprise the steps of (a) reacting a truncated GDNF protein with polyethylene glycol (such as a reactive ester or aldehyde derivative of PEG) under conditions whereby the truncated GDNF protein becomes attached to one or more PEG groups, and (b) obtaining the reaction product(s). In general, the optimal reaction conditions for the acylation reactions will be determined case-by-case based on known parameters and the desired result. For example, the larger the ratio of PEG:protein, the greater the percentage of poly-pegylated product. The optimum ratio (in terms of efficiency of reaction in that there is no excess unreacted protein or polymer) may be determined by factors such as the desired degree of derivatization (e.g., mono-, di-, tri-, etc.), the molecular weight of the polymer selected, whether the polymer is branched or unbranched, and the reaction conditions used.

Reductive alkylation to produce a substantially homogeneous population of mono-polymer/truncated GDNF protein conjugate will generally comprise the steps of (a) reacting a truncated GDNF protein with a reactive PEG molecule under reductive alkylation conditions, at a pH suitable to permit selective modification of the α-amino group at the amino terminus of the truncated GDNF protein, and (b) obtaining the reaction product(s).

For a substantially homogeneous population of mono-polymer/truncated GDNF protein conjugate, the reductive alkylation reaction conditions are those which permit the selective attachment of the water soluble polymer moiety to the N-terminus of a truncated GDNF protein. Such reaction conditions generally provide for $pK_a$ differences between the lysine amino groups and the at-amino group at the N-terminus (the $pK_a$ being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal α-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3-9, preferably 3-6.

Another consideration is the molecular weight of the polymer. In general, the higher the molecular weight of the polymer, the fewer the number of polymer molecules which may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2 kDa to about 100 kDa (the term "about" indicating that in preparations of polyethylene glycol, some molecules will weigh more, some less, than the stated molecular weight). The preferred average molecular weight is about 5 kDa to about 50 kDa, particularly preferably about 12 kDa to about 25 kDa. The ratio of water-soluble polymer to truncated GDNF protein will generally range from 1:1 to 100:1, preferably (for polypegylation) 1:1 to 20:1, and (for mono-pegylation) 1:1 to 5:1.

Using the conditions indicated above, reductive alkylation will provide for selective attachment of the polymer to any truncated GDNF protein having an αamino group at the amino terminus, and provide for a substantially homogenous preparation of mono-polymer/truncated GDNF protein conjugate. The term "mono-polymer/truncated GDNF protein conjugate" is used here to mean a derivative containing a single polymer molecule attached to a truncated GDNF protein. The mono-polymer/truncated GDNF protein conjugate preferably will have a polymer molecule located at the N-terminus, but not on lysine amino side groups. The preparation will preferably be greater than 90% mono-polymer/truncated GDNF protein conjugate, and more preferably greater than 95% mono-polymer/truncated GDNF protein conjugate, with the remainder of observable proteins being unreacted (i.e., protein lacking the polymer moiety).

For reductive alkylation, the reducing agent should be stable in aqueous solution and preferably be able to reduce only the Schiff base formed in the initial process of reductive alkylation. Exemplary reducing agents may be selected from the group consisting of sodium borohydride, sodium cyanoborohydride, dimethylamine borane, trimethylamine borane and pyridine borane. A particularly preferred reducing agent is sodium cyanoborohydride. Other reaction parameters, such as solvent, reaction times, temperatures, etc., and means of purification of products, can be determined case-by-case based on commonly available information relating to derivatization of proteins with water soluble polymers.

One may choose to prepare a mixture of polymer/protein conjugates by acylation and/or alkylation methods, and the advantage provided herein is that one may select the proportion of mono-polymer/protein conjugate to include in the mixture. Thus, if desired, one may prepare a mixture of protein having various numbers of polymer molecules attached thereto (i.e., di-, tri-, tetra-, etc.) and combine with the mono-polymer/protein conjugate material prepared using the present methods, and have a mixture with a predetermined proportion of mono-polymer/protein conjugate.

Polynucleotides Encoding Truncated GDNF Proteins

The present invention further provides novel polynucleotides which encode truncated GDNF proteins. When used as a hybridization probe or amplification primer, the nucleic acid sequence will be substantially free from all other nucleic acid sequences. For use in recombinant protein expression, the nucleic acid sequence will generally be substantially free from nucleic acid sequences encoding other proteins, unless a fusion protein is intended. Based upon the present description and using the universal codon table, one of ordinary skill in the art can readily determine all of the nucleic acid sequences which encode the amino acid sequences of truncated GDNF proteins. Presently preferred nucleic acid sequences include those polynucleotides encoding the $[Arg^{16}\text{-}Ile^{134}]$, $[Ser^{26}\text{-}Ile^{134}]$, $[Arg^{32}\text{-}Ile^{134}]$, and $[Lys^{37}\text{-}Ile^{134}]$ truncated GDNF proteins. Examples of a variety of polynucleotides are depicted in FIGS. 5, 6 and 7 as well as those portions of FIGS. 1, 3 and 4 which encode truncated GDNF proteins. It will also be appreciated by those skilled in the art that the novel polynucleotides which encode truncated GDNF proteins include those nucleic acid sequences encoding variant truncated GDNF proteins, whether man-made or naturally occurring.

Recombinant expression techniques, conducted in accordance with the descriptions set forth below, may be followed to produce these polynucleotides and express the various truncated GDNF proteins. For example, by inserting a nucleic acid sequence which encodes a truncated GDNF protein into an appropriate vector, one skilled in the art can readily produce large quantities of the desired nucleotide sequence. The sequences can then be used to generate detection probes or amplification primers. Alternatively, a polynucleotide encoding a truncated GDNF protein can be inserted into an expression vector. By introducing the expression vector into an appropriate host, the desired truncated GDNF protein may be produced in large amounts.

As further described herein, there are numerous host/vector systems available for the propagation of nucleic acid sequences and/or the production of truncated GDNF proteins. These include, but are not limited to, plasmid, viral and insertional vectors, and prokaryotic and eukaryotic hosts. One skilled in the art can adapt a host/vector system which is capable of propagating or expressing heterologous DNA to produce or express the sequences of the present invention.

By means of such recombinant techniques, the truncated GDNF proteins of the present invention are readily produced in commercial quantities. Furthermore, it will be appreciated by those skilled in the art that, in view of the present disclosure, the novel nucleic acid sequences include degenerate nucleic acid sequences encoding the truncated GDNF proteins specifically set forth in the Figures, variants of such truncated GDNF proteins, and those nucleic acid sequences which hybridize, preferably under stringent hybridization conditions, to complements of these nucleic acid sequences (see, Maniatis et. al., *Molecular Cloning* (A Laboratory Manual); Cold Spring Harbor Laboratory, pages 387 to 389, 1982.) Exemplary stringent hybridization conditions are hybridization in 4×SSC at 62-67° C., followed by washing in 0.1×SSC at 62-67° C. for approximately an hour. Alternatively, exemplary stringent hybridization conditions are hybridization in 45-55% formamide, 4×SSC at 40-45° C. DNA sequences which hybridize to the complementary sequences for truncated GDNF protein under relaxed hybridization conditions and which encode a truncated GDNF protein of the present invention are also included herein. Examples of such relaxed stringency hybridization conditions are 4×SSC at 45-55° C. or hybridization with 30-40% formamide at 40-45° C.

Also provided by the present invention are recombinant DNA constructs involving vector DNA together with the DNA sequence encoding a truncated GDNF protein. In such DNA constructs, the nucleic acid sequence encoding truncated GDNF protein (with or without signal peptides) is in operative association with a suitable expression control or regulatory sequence capable of directing the replication and/or expression of the truncated GDNF protein in a selected host.

Recombinant Expression of Truncated GDNF Protein

Preparation of Polynucleotides Encoding Truncated GDNF

A nucleic acid sequence encoding truncated GDNF, or a mature GDNF starting material, can readily be obtained in a variety of ways, including, without limitation, chemical synthesis, cDNA or genomic library screening, expression library screening, and/or PCR amplification of cDNA. These methods and others useful for isolating such nucleic acid sequences are set forth, for example, by Sambrook et al. (*Molecular Cloning: A Laboratory Manual*, Cold Spring Harbor Laboratory Press, Cold Spring Harbor, N.Y., 1989), by Ausubel et al., eds (*Current Protocols in Molecular Biology*, Current Protocols Press, 1994), and by Berger and Kimmel (*Methods in Enzymology: Guide to Molecular Cloning Techniques*, vol. 152, Academic Press, Inc., San Diego, Calif., 1987). Preferred nucleic acid sequences encoding GDNF are mammalian sequences.

Chemical synthesis of a nucleic acid sequence which encodes a truncated GDNF protein can also be accomplished using methods well known in the art, such as those set forth by Engels et al. (*Angew. Chem. Intl. Ed.*, 28:716-734,1989). These methods include, inter alia, the phosphotriester, phosphoramidite and H-phosphonate methods of nucleic acid sequence synthesis. The nucleic acid sequence encoding the truncated GDNF protein will be several hundred base pairs (bp) or nucleotides in length. Large nucleic acid sequences, for example those larger than about 100 nucleotides in length, can be synthesized as several fragments. The fragments can then be ligated together to form a nucleic acid sequence encoding truncated GDNF protein. A preferred method is polymer-supported synthesis using standard phosphoramidite chemistry.

Alternatively, a suitable nucleic acid sequence may be obtained by screening an appropriate cDNA library (i.e., a library prepared from one or more tissue source(s) believed to express the protein) or a genomic library (a library prepared from total genomic DNA). The source of the cDNA library is typically a tissue from any species that is believed to express GDNF in reasonable quantities. The source of the genomic library may be any tissue or tissues from any mammalian or other species believed to harbor a gene encoding GDNF or a GDNF homologue. The library can be screened for the presence of the GDNF cDNA/gene using one or more nucleic acid probes (oligonucleotides, cDNA or genomic DNA fragments that possess an acceptable level of homology to the GDNF or GDNF homologue cDNA or gene to be cloned) that will hybridize selectively with GDNF or GDNF homologue cDNA(s) or gene(s) present in the library. The probes typically used for such library screening usually encode a small region of the GDNF DNA sequence from the same or a similar species as the species from which the library was prepared. Alternatively, the probes may be degenerate, as discussed herein.

Library screening is typically accomplished by annealing the oligonucleotide probe or cDNA to the clones in the library under conditions of stringency that prevent non-specific binding but permit binding of those clones that have a significant level of homology with the probe or primer. Typical hybridization and washing stringency conditions depend in part on the size (i.e., number of nucleotides in length) of the cDNA or oligonucleotide probe, and whether the probe is degenerate. The probability of obtaining a clone(s) is also considered in designing the hybridization solution (i.e., whether a cDNA or genomic library is being screened; if it is a cDNA library, the probability that the cDNA of interest is present at a high level).

Where DNA fragments (such as cDNAs) are used as probes, typical hybridization conditions include those as set forth in Ausubel et al., eds., supra. After hybridization, the blot containing the library is washed at a suitable stringency, depending on several factors such as probe size, expected homology of probe to clone, type of library being screened, number of clones being screened, and the like. Examples of stringent washing solutions (which are usually low in ionic strength and are used at relatively high temperatures) are as follows. One such stringent wash is 0.015 M NaCl, 0.005 M NaCitrate and 0.1% SDS at 55-65° C. Another such stringent buffer is 1 mM $Na_2EDTA$, 40 mM $NaHPO_4$, pH 7.2, and 1% SDS at about 40-50° C. One other stringent wash is 0.2×SSC and 0.1% SDS at about 50-65° C.

There are also exemplary protocols for stringent washing conditions where oligonucleotide probes are used to screen cDNA or genomic libraries. For example, a first protocol uses 6×SSC with 0.05 percent sodium pyrophosphate at a temperature of between about 35 and 62° C., depending on the length of the probe. For example, 14 base probes are washed at 35-40° C., 17 base probes at 45-50° C., 20 base probes at 52-57° C., and 23 base probes at 57-63° C. The temperature can be increased 2-3° C. where the background non-specific binding appears high. A second protocol uses tetramethylammonium chloride (TMAC) for washing. One such stringent washing solution is 3 M TMAC, 50 mM Tris-HCl, pH 8.0, and 0.2% SDS.

Another suitable method for obtaining a nucleic acid sequence encoding a GDNF protein is the polymerase chain reaction (PCR). In this method, poly(A)+RNA or total RNA is extracted from a tissue that expresses GDNF. cDNA is then prepared from the RNA using the enzyme reverse transcriptase. Two primers, typically complementary to two separate regions of the GDNF cDNA (oligonucleotides), are then added to the cDNA along with a polymerase such as Taq polymerase, and the polymerase amplifies the cDNA region between the two primers.

Where the method of choice for preparing the nucleic acid sequence encoding the desired truncated GDNF protein requires the use of oligonucleotide primers or probes (e.g., PCR, cDNA or genomic library screening), the oligonucleotide sequences selected as probes or primers should be of adequate length and sufficiently unambiguous so as to minimize the amount of non-specific binding that will occur during library screening or PCR amplification. The actual sequence of the probes or primers is usually based on conserved or highly homologous sequences or regions from the same or a similar gene from another organism. Optionally, the probes or primers can be fully or partially degenerate, i.e., contain a mixture of probes/primers, all encoding the same amino acid sequence, but using different codons to do so. An alternative to preparing degenerate probes is to place an inosine in some or all of those codon positions that vary by species. The oligonucleotide probes or primers may be prepared by chemical synthesis methods for DNA as described above.

Truncated GDNF proteins based on these nucleic acid sequences encoding GDNF, as well as mutant or variant sequences thereof, are also contemplated as within the scope of the present invention. As described above, a mutant or variant sequence is a sequence that contains one or more nucleotide substitutions, deletions, and/or insertions as compared to the wild type sequence and that results in the expression of amino acid sequence variations as compared to the wild type amino acid sequence. In some cases, naturally occurring GDNF amino acid mutants or variants may exist, due to the existence of natural allelic variation. Truncated GDNF proteins based on such naturally occurring mutants or variants are also within the scope of the present invention. Preparation of synthetic mutant sequences is also well known in the art, and is described for example in Wells et al. (*Gene*, 34:315, 1985) and in Sambrook et al., supra.

Vectors

The cDNA or genomic DNA encoding a truncated GDNF protein is inserted into a vector for further cloning (amplification of the DNA) or for expression. Suitable vectors are commercially available, or the vector may be specially constructed. The selection or construction of the appropriate vector will depend on 1) whether it is to be used for DNA amplification or for DNA expression, 2) the size of the DNA to be inserted into the vector, and 3) the host cell (e.g., mammalian, insect, yeast, fungal, plant or bacterial cells) to be transformed with the vector. Each vector contains various components depending on its function (amplification of DNA or expression of DNA) and its compatibility with the intended host cell. The vector components generally include, but are not limited to, one or more of the following: a signal sequence, an origin of replication, one or more selection or marker genes, enhancer elements, promoters, a transcription termination sequence, and the like. These components may be obtained from natural sources or synthesized by known procedures. The vectors of the present invention involve a nucleic acid sequence which encodes the truncated GDNF protein of interest operatively linked to one or more of the following expression control or regulatory sequences capable of directing, controlling or otherwise effecting the expression of the truncated GDNF protein by a selected host cell.

Signal Sequence

The signal sequence may be a component of the vector, or it may be a part of GDNF DNA that is inserted into the vector. The native GDNF DNA encodes a signal sequence at the amino terminus of the protein that is cleaved during post-translational processing of the protein to form the mature GDNF protein. Included within the scope of this invention are truncated GDNF polynucleotides with the native signal sequence and other pre-pro sequences as well as truncated GDNF polynucleotides wherein the native signal sequence is deleted and replaced with a heterologous signal sequence. The heterologous signal sequence selected should be one that is recognized and processed, i.e., cleaved by a signal peptidase, by the host cell. For prokaryotic host cells that do not recognize and process the native GDNF signal sequence, the signal sequence is substituted by a prokaryotic signal sequence selected, for example, from the group of the alkaline phosphatase, penicillinase, or heat-stable enterotoxin II leaders. For yeast secretion, the native GDNF signal sequence may be substituted by the yeast invertase, alpha factor, or acid phosphatase leaders. In mammalian cell expression the native signal sequence is satisfactory, although other mammalian signal sequences may be suitable.

Origin of Replication

Expression and cloning vectors generally include a nucleic acid sequence that enables the vector to replicate in one or more selected host cells. In cloning vectors, this sequence is typically one that enables the vector to replicate independently of the host chromosomal DNA, and includes origins of replication or autonomously replicating sequences. Such sequences are well known for a variety of bacteria, yeasts, and viruses. The origin of replication from the plasmid pBR322 is suitable for most Gram-negative bacteria and various origins (e.g., SV40, polyoma, adenovirus, VSV or BPV) are useful for cloning vectors in mammalian cells. Generally, the origin of replication component is not needed for mammalian expression vectors (for example, the SV40 origin is often used only because it contains the early promoter).

Selection Gene

The expression and cloning vectors typically contain a selection gene. This gene encodes a "marker" protein necessary for the survival or growth of the transformed host cells when grown in a selective culture medium. Host cells that were not transformed with the vector will not contain the selection gene, and therefore, they will not survive in the culture medium. Typical selection genes encode proteins that (a) confer resistance to antibiotics or other toxins, e.g., ampicillin, neomycin, methotrexate, or tetracycline; (b) complement auxotrophic deficiencies; or (c) supply critical nutrients not available from the culture medium.

Other selection genes may be used to amplify the gene which will be expressed. Amplification is the process wherein genes which are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure which only the transformants are uniquely adapted to survive by virtue of the marker present in the vector. Selection pressure is imposed by culturing the transformed cells under conditions in which the concentration of selection agent in the medium is successively changed, thereby leading to amplification of both the selection gene and the DNA that encodes truncated GDNF. As a result, increased quantities of truncated GDNF are synthesized from the amplified DNA.

For example, cells transformed with the DHFR selection gene are first identified by culturing all of the transformants in a culture medium that contains methotrexate, a competitive antagonist of DHFR. An appropriate host cell when wild-type DHFR is used is the Chinese hamster ovary cell line deficient in DHFR activity (see, for example, Urlaub and Chasin, *Proc. Natl. Acad. Sci., USA* 77 (7): 4216-4220 (1980)). The transformed cells are then exposed to increased levels of methotrexate. This leads to the synthesis of multiple copies of the DHFR gene, and, concomitantly, multiple copies of other DNA present in the expression vector, such as the DNA encoding a truncated GDNF protein.

Promoter

The expression and cloning vectors of the present invention will typically contain a promoter that is recognized by the host organism and operably linked to the nucleic acid sequence encoding the truncated GDNF protein. Promoters are untranslated sequences located upstream (5') to the start codon of a structural gene (generally within about 100 to 1000 bp) that control the transcription and translation of a particular nucleic acid sequence, such as that encoding truncated GDNF. Promoters are conventionally grouped into one of two classes, inducible promoters and constitutive promoters. Inducible promoters initiate increased levels of transcription from DNA under their control in response to some change in culture conditions, such as the presence or absence of a nutrient or a change in temperature. A large number of promoters, recognized by a variety of potential host cells, are well known. These promoters are operably linked to the DNA encoding truncated GDNF by removing the promoter from the source DNA by restriction enzyme digestion and inserting the desired promoter sequence into the vector. The native GDNF promoter sequence may be used to direct amplification and/or expression of truncated GDNF DNA. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase, a tryptophan (trp) promoter system; and hybrid promoters such as the tac promoter. Other known bacterial promoters are also suitable. Their nucleotide sequences have been published, thereby enabling one skilled in the art to ligate them to the desired DNA sequence(s), using linkers or adaptors as needed to supply any required restriction sites.

Suitable promoting sequences for use with yeast hosts are also well known in the art. Yeast enhancers are advantageously used with yeast promoters. Suitable promoters for use with mammalian host cells are well known and include those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40). Other suitable mammalian promoters include heterologous mammalian promoters, e.g., heat-shock promoters and the actin promoter. A currently used promoter in the production of GDNF proteins in CHO cells is SRα. See Takebe et al., *Mol. Cell. Biol.* 8 (1): 466-472 (1988). A suitable expression vector is pDSRα2, which is further described below.

Enhancer Element

An enhancer sequence may be inserted into the vector to increase the transcription of a DNA sequence encoding a truncated GDNF protein of the present invention by higher eukaryotes. Enhancers are cis-acting elements of DNA, usually about from 10-300 bp in length, that act on the promoter to increase its transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to truncated GDNF DNA, it is typically located at a site 5' from the promoter.

Transcription Termination

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and occasionally 3' untranslated regions of eukaryotic DNAs or cDNAs. These regions contain nucleotide segments transcribed as polyadenylated fragments in the untranslated portion of the mRNA encoding truncated GDNF.

The construction of suitable vectors containing one or more of the above-listed components together with the desired truncated GDNF coding sequence is accomplished by standard ligation techniques. Isolated plasmids or DNA fragments are cleaved, tailored, and religated in the desired order to generate the plasmids required. To confirm that the correct sequences have been constructed, the ligation mixtures may be used to transform *E. coli,* and successful transformants may be selected by known techniques, such as ampicillin or tetracycline resistance as described above. Plasmids from the transformants are then prepared, analyzed by restriction endonuclease digestion, and/or sequenced to confirm the presence of the desired construct.

Vectors that provide for the transient expression of DNA encoding truncated GDNF in mammalian cells may also be used. In general, transient expression involves the use of an expression vector that is able to replicate efficiently in a host cell, such that the host cell accumulates many copies of the expression vector and, in turn, synthesizes high levels of the desired protein encoded by the expression vector. Transient expression systems, comprising a suitable expression vector and a host cell, allow for the convenient positive identification of proteins encoded by cloned DNAs, as well as for the rapid screening of such proteins for desired biological or physiological properties. Thus, transient expression systems are particularly useful in identifying variants of the protein.

Selection and Transformation of Host Cells

Host cells (e.g., bacterial, mammalian, insect, yeast, or plant cells) transformed with nucleic acid sequences for use in expressing a recombinant truncated GDNF protein are also provided by the present invention. The transformed host cell is cultured under appropriate conditions permitting the expression of the nucleic acid sequence. The selection of suitable host cells and methods for transformation, culture, amplification, screening and product production and purification are well known in the art. See for example, Gething and Sambrook, *Nature* 293: 620-625 (1981), or alternatively, Kaufman et al., *Mol. Cell. Biol.,* 5 (7): 1750-1759 (1985) or Howley et al., U.S. Pat. No. 4,419,446. Truncated GDNF may be expressed in *E. coil* in accordance with the description of Lin et al. (U.S. patent application Ser. No. 07/855,413, now abandoned; Application No. PCT/US92/07888; WO 93/06116) which involved the expression of mature GDNF. Other exemplary materials and methods are discussed in further detail below. The transformed host cell is cultured in a suitable medium, and the expressed factor is then optionally recovered, isolated and purified from the culture medium (or from the cell, if expressed intracellularly) by an appropriate means known to those skilled in the art.

Suitable host cells for cloning or expressing the vectors herein are the prokaryote, yeast, or higher eukaryote cells as described above. Prokaryotic host cells include, but are not limited to, eubacteria, such as Gram-negative or Gram-positive organisms, for example, *E. coli, Bacilli* such as *B. subtilis, Pseudomonas* species such as *P. aeruginosa, Salmonella typhimurium,* or *Serratia marcescans.* Alternatively, in vitro methods of cloning, e.g., PCR or other nucleic acid polymerase reactions, are suitable.

In addition to prokaryotic host cells, eukaryotic microbes such as filamentous fungi or yeast may be suitable hosts for the expression of truncated GDNF proteins. *Saccharomyces*

*cerevisiae,* or common baker's yeast, is the most commonly used among lower eukaryotic host microorganisms, but a number of other genera, species, and strains are well known and commonly available.

Suitable host cells for the expression of glycosylated truncated GDNF protein are derived from multicellular organisms. Such host cells are capable of complex processing and glycosylation activities. In principle, any higher eukaryotic cell culture might be used, whether such culture involves vertebrate or invertebrate cells, including plant and insect cells. Vertebrate cells are generally used as the propagation of vertebrate cells in culture (tissue culture) is a well known procedure. Examples of useful mammalian host cell lines include, but are not limited to, monkey kidney CV1 line transformed by SV40 (COS-7), human embryonic kidney line (293 or 293 cells subcloned for growth in suspension culture), baby hamster kidney cells, and Chinese hamster ovary cells. Other suitable mammalian cell lines include but are not limited to, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, DH5α, DH10, and MC1061) are well-known as host cells in the field of biotechnology. Various strains of *Streptomyces* spp. and the like may also be employed. Presently preferred host cells for producing truncated GDNF proteins are bacterial cells (e.g., *Escherichia coli*) and mammalian cells (such as Chinese hamster ovary cells, COS cells, etc.)

The host cells are transfected and preferably transformed with the above-described expression or cloning vectors and cultured in a conventional nutrient medium. The medium may be modified as appropriate for inducing promoters, selecting transformants, or amplifying the genes encoding the desired sequences. Transfection and transformation are performed using standard techniques which are well known to those skilled in the art and which are selected as appropriate to the host cells involved. For example, for mammalian cells without cell walls, the calcium phosphate precipitation method may be used. Electroporation, micro injection and other known techniques may also be used.

Culturing the Host Cells

Transformed cells used to produce truncated GDNF proteins of the present invention are cultured in suitable media. The media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamicin), trace elements (defined as inorganic compounds usually present at final concentrations in the micromolar range), and glucose or other energy source. Other supplements may also be included, at appropriate concentrations, as will be appreciated by those skilled in the art. Suitable culture conditions, such as temperature, pH, and the like, are also well known to those skilled in the art for use with the selected host cells.

It is also possible that truncated GDNF proteins may be produced by homologous recombination, or with recombinant production methods utilizing control elements introduced into cells already containing DNA encoding GDNF. Homologous recombination is a technique originally developed for targeting genes to induce or correct mutations in transcriptionally active genes (Kucherlapati, *Prog. in Nuc. Acid Res. and Mol. Biol.* 36:301 (1989)). The basic technique was developed as a method for introducing specific mutations into specific regions of the mammalian genome (Thomas et al., *Cell.* 44:419-428,1986; Thomas and Capecchi, *Cell.* 51:503-512,1987; Doetschman et al., *Proc. Natl. Acad. Sci.* 85:8583-8587, 1988) or to correct specific mutations within defective genes (Doetschman et al., *Nature.* 330:576-578, 1987). Exemplary homologous recombination techniques are described in U.S. Pat. No. 5,272,071 (EP 91 90 3051, EP Publication No. 505 500; PCT/US90/07642, International Publication No. WO 91/09955) the disclosure of which is hereby incorporated by reference.

Through homologous recombination, the DNA sequence to be inserted into the genome can be directed to a specific region of the gene of interest by attaching it to targeting DNA. The targeting DNA is DNA that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize and therefore recombine with other pieces of endogenous DNA through shared homologous regions. If this complementary strand is attached to an oligonucleotide that contains a mutation or a different sequence of DNA, it too is incorporated into the newly synthesized strand as a result of the recombination. As a result of the proofreading function, it is possible for the new sequence of DNA to serve as the template. Thus, the transferred DNA is incorporated into the genome.

If the sequence of a particular gene is known, such as the nucleic acid sequence of GDNF, the pre-pro sequence or expression control sequence, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be backstitched into the newly synthesized daughter strand of DNA.

In the present invention, attached to these pieces of targeting DNA are regions of DNA which may interact with the expression of a GDNF protein. For example, a promoter/enhancer element, a suppresser, or an exogenous transcription modulatory element is inserted in the genome of the intended host cell in proximity and orientation sufficient to influence the transcription of DNA encoding the desired truncated GDNF. The control element does not encode truncated GDNF, but instead controls a portion of the DNA present in the host cell genome. Thus, the expression of truncated GDNF proteins may be achieved not by transfection of DNA that encodes the truncated GDNF gene itself, but rather by the use of targeting DNA (containing regions of homology with the endogenous gene of interest) coupled with DNA regulatory segments that provide the endogenous gene sequence with recognizable signals for transcription of a truncated GDNF protein.

In accordance with the present invention, homologous recombination methods may also be used to modify a cell that contains a normally transcriptionally silent GDNF gene to produce a cell which expresses GDNF. The GDNF protein may then be processed to form a truncated GDNF protein(s).

Truncated GDNF Pharmaceutical Compositions

Truncated GDNF protein product pharmaceutical compositions typically include a therapeutically effective amount of a truncated GDNF protein product in admixture with one or more pharmaceutically and physiologically acceptable formulation materials. Suitable formulation materials include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle may be water for injection, physiological saline solution, or artificial cerebrospinal fluid (CSF), possibly supplemented with other materials common in compositions for parenteral administration. Neutral buffered saline or saline mixed with serum albumin are further exemplary vehicles.

The primary solvent in a vehicle may be either aqueous or non-aqueous in nature. In addition, the vehicle may contain other pharmaceutically-acceptable excipients for modifying or maintaining the pH, osmolarity, viscosity, clarity, color, sterility, stability, rate of dissolution, or odor of the formulation. Similarly, the vehicle may contain still other pharmaceutically-acceptable excipients for modifying or maintaining the stability, rate of dissolution, or rate of release of truncated GDNF protein product, or for promoting the absorption or penetration of truncated GDNF protein product across the blood-brain barrier. Such excipients are those substances usually and customarily employed to formulate dosages for parenteral administration in either unit dose or multi-dose form or for direct infusion into the CSF by continuous or periodic infusion from an implanted pump.

Once the therapeutic composition has been formulated, it may be stored in sterile vials as a solution, suspension, gel, emulsion, solid, or dehydrated or lyophilized powder. Such formulations may be stored either in a ready to use form or in a form, e.g., lyophilized, requiring reconstitution prior to administration.

The optimal pharmaceutical formulation will be determined by one skilled in the art depending upon the route of administration and desired dosage. See for example, *Remington's Pharmaceutical Sciences,* 18th Ed. (1990, Mack Publishing Co., Easton, Pa. 18042) pages 1435-1712 the disclosure of which is hereby incorporated by reference. The composition may also involve particulate preparations of polymeric compounds such as polylactic acid, polyglycolic acid, etc. or into liposomes. Hylauronic acid may also be used, and this may have the effect of promoting sustained duration in the circulation. Such compositions may influence the physical state, stability, rate of in vivo release, and rate of in vivo clearance of the present proteins and derivatives.

Other effective administration forms, such as parenteral slow-release formulations, inhalant mists, orally active formulations, or suppositories, are also envisioned. Current truncated GDNF protein product pharmaceutical compositions are formulated for parenteral administration, e.g., intracerebroventricular injection. Such parenterally administered therapeutic compositions are typically in the form of a pyrogen-free, parenterally acceptable aqueous solution comprising truncated GDNF protein product in a pharmaceutically acceptable vehicle. One preferred vehicle is physiological saline.

It is also contemplated that certain formulations containing truncated GDNF protein product are to be administered orally. Truncated GDNF protein product which is administered in this fashion may be encapsulated and may be formulated with or without those carriers customarily used in the compounding of solid dosage forms. The capsule may designed to release the active portion of the formulation at the point in the gastrointestinal tract when bioavailability is maximized and pre-systemic degradation is minimized.

Additional excipients may be included to facilitate absorption of truncated GDNF protein product. Diluents, flavorings, low melting point waxes, vegetable oils, lubricants, suspending agents, tablet disintegrating agents, and binders may also be employed.

Administration of Truncated GDNF Protein Product

The truncated GDNF protein product may be administered parenterally via a subcutaneous, intramuscular, intravenous, transpulmonary, transdermal, intrathecal or intracerebral route. Protein growth factors that do not cross the blood-brain barrier may be given directly intracerebrally or otherwise in association with other elements that will transport them across the barrier. It is preferred that the truncated GDNF protein product is administered intracerebroventricularly or into the brain or spinal cord subarachnoid space. Truncated GDNF protein product may also be administered intracerebrally directly into the brain parenchyma. Slow-releasing implants in the brain containing the neurotrophic factor embedded in a biodegradable polymer matrix can also deliver truncated GDNF protein product. Truncated GDNF protein product may be administered extracerebrally in a form that has been modified chemically or packaged so that it passes the blood-brain barrier, or it may be administered in connection with one or more agents capable of promoting penetration of truncated GDNF protein product across the barrier. For example, a conjugate of NGF and monoclonal anti-transferrin receptor antibodies has been shown to be transported to the brain via binding to transferrin receptors. To achieve the desired dose of truncated GDNF protein product, repeated daily or less frequent injections may be administered, or truncated GDNF protein product may be infused continuously or periodically from a constant-or programmable-flow implanted pump. The frequency of dosing will depend on the pharmacokinetic parameters of the truncated GDNF protein product as formulated, and the route of administration.

Regardless of the manner of administration, the specific dose is typically calculated according to body weight or body surface area. For diseases involving the brain, the specific dose is typically calculated according to the approximate brain weight of the patient, which also may be estimated based on body weight or body surface area. Further refinement of the calculations necessary to determine the appropriate dosage for treatment involving each of the above mentioned formulations is routinely made by those of ordinary skill in the art, especially in light of the dosage information and assays disclosed herein. Appropriate dosages may be ascertained through use of the established assays for determining dosages utilized in conjunction with appropriate dose-response data. The final dosage regimen involved in a method of treating a specific condition will be determined by the attending physician, considering various factors which modify the action of drugs, e.g., the age, condition, body weight, sex and diet of the patient, the severity of any infection, time of administration and other clinical factors.

Truncated GDNF protein product of the present invention may also be employed, alone or in combination with other growth factors in the treatment of nerve disease. For example, truncated GDNF protein product may be used in treating some forms of nerve disease in combination with nerve growth factor. In addition, other factors or other molecules, including chemical compositions, may be employed together with truncated GDNF protein product. In the treatment of Parkinson's Disease, it is contemplated that truncated GDNF protein product be used by itself or in conjunction with the administration of Levodopa, wherein the truncated GDNF would enhance the production of endogenous dopamine and the neuronal uptake of the increased concentration of dopamine.

As stated above, it is also contemplated that additional neurotrophic or neuron nurturing factors will be useful or necessary to treat some neuronal cell populations or some types of injury or disease. Other factors that may be used in conjunction with truncated GDNF include, but are not limited to: mitogens such as insulin, insulin-like growth factors, epidermal growth factor, vasoactive growth factor, pituitary adenylate cyclase activating polypeptide, interferon and somatostatin; neurotrophic factors such as brain derived neurotrophic factor, neurotrophin-3, neurotrophin-4/5, neurotrophin-6, insulin-like growth factor, ciliary neurotrophic factor, acidic and basic fibroblast growth factors, fibroblast growth factor-5, transforming growth factor-β, cocaine-amphetamine regulated transcript (CART) and mature GDNF; and other growth factors such as epidermal growth factor, leukemia inhibitory factor, interleukins, interferons, and colony stimulating factors; as well as molecules and materials which are the functional equivalents to these factors.

It is envisioned that the continuous administration or sustained delivery of a truncated GDNF protein product may be advantageous for a given treatment. While continuous administration may be accomplished via a mechanical means, such as with an infusion pump, it is contemplated that other modes of continuous or near continuous administration may be practiced. For example, chemical derivatization may result in sustained release forms of the protein which have the effect of continuous presence in the blood stream, in predictable amounts, based on a determined dosage regimen. Thus, truncated GDNF protein products include truncated GDNF protein derivatized to effectuate such continuous administration.

Truncated GDNF protein cell therapy, e.g., intracerebral implantation of cells producing truncated GDNF protein, is also contemplated. This embodiment of the present invention may include implanting into patients cells which are capable of synthesizing and secreting a biologically active form of truncated GDNF protein. Such truncated GDNF protein producing-cells may be cells which do not normally produce a neurotrophic factor but have been modified to produce truncated GDNF, or they could be cells whose ability to produce GDNF has been augmented by transformation with a polynucleotide suitable for the expression and secretion of truncated GDNF protein. In order to minimize a potential immunological reaction in patients from administering GDNF of a foreign species, it is preferred that the cells be of human origin and produce truncated human GDNF protein.

Implanted cells may be encapsulated to avoid infiltration of the cells into brain tissue. Human or non-human animal cells may be implanted in patients in biocompatible, semi-permeable polymeric enclosures or membranes to allow release of a truncated GDNF protein product, but that prevent destruction of the cells by the patient's immune system or by other detrimental factors from the surrounding tissue. Alternatively, the patient's own cells, transformed ex vivo to produce truncated GDNF, could be implanted directly into the patient without such encapsulation.

The methodology for the membrane encapsulation of living cells is familiar to those of ordinary skill in the art, and the preparation of the encapsulated cells and their implantation in patients may be accomplished. See for example, U.S. Pat. Nos. 4,892,538; 5,011,472; and 5,106,627, the disclosures of which are hereby incorporated by reference. A system for encapsulating living cells is also described in PCT Application WO 91/10425 of Aebischer et al., specifically incorporated herein by reference. See also, PCT Application WO 91/10470 of Aebischer et al.; Winn et al., *Exper. Neurol.*, 113:322-329, 1991; Aebischer et al., *Exper. Neurol.*, 11 1:269-275,1991; Tresco et al., *ASAIO*, 38:17-23, 1992, the disclosures of which are hereby incorporated by reference.

Truncated GDNF protein gene therapy in vivo is also envisioned, wherein a nucleic acid sequence encoding a truncated GDNF protein is introduced directly into the patient. For example, a nucleic acid sequence encoding a truncated GDNF protein is introduced into target cells via local injection of a nucleic acid construct with or without an appropriate delivery vector, such as an adeno-associated virus vector. Alternative viral vectors include, but are not limited to, retrovirus, adenovirus, herpes simplex virus and papilloma virus vectors. Physical transfer may be achieved in vivo by local injection of the desired nucleic acid construct or other appropriate delivery vector containing the desired nucleic acid sequence, liposome-mediated transfer, direct injection (naked DNA), receptor-mediated transfer (ligand-DNA complex), or microparticle bombardment (gene gun).

It should be noted that the truncated GDNF protein product formulations described herein may be used for veterinary as well as human applications and that the term "patient" should not be construed in a limiting manner. In the case of veterinary applications, the dosage ranges should be the same as specified above.

As a means of further characterizing truncated GDNF proteins of the present invention, antibodies can be developed which bind to the truncated GDNF protein such as to epitopes within the X-[$Cys^{41}$-$Cys^{133}$]-Y amino acid sequence. One of ordinary skill in the art can use well-known, published procedures to obtain monoclonal and polyclonal antibodies, or recombinant antibodies, which specifically recognize and bind to the various proteins encoded by the amino acid sequences of the present invention. Such antibodies may then be used to purity and characterize truncated GDNF protein. Alternatively, the antibodies may be used as therapeutical inhibitors of the proteins to which they are directed.

Other aspects and advantages of the present invention will be understood upon consideration of the following illustrative examples. Example 1 addresses the expression of mature GDNF in a mammalian cell system and the preparation of truncated GDNF protein. Example 2 addresses the expression of mature GDNF in a bacterial cell system. Example 3 addresses the expression of various truncated GDNF proteins in a bacterial cell system. Example 4 compares the biological activity of the mature GDNF protein and truncated GDNF protein in an assay for dopaminergic neuron neurotrophic activity.

EXAMPLES

Example 1

Expression of Mature Human GDNF in CHO Cells and the Purification of CHO Cell-Derived Truncated GDNF Protein Materials The following materials are used in the expression of human GDNF in dihydrofolate reductase-deficient CHO cells (CHOd⁻ cells; for example, as described by Urlaub and Chasin, *Proc. Natl. Acad. Sci., USA* 77 (7): 4216-4220 (1980)).

CHOd⁻ medium contained: Dulbecco's Modified Eagle's Medium (DMEM)—high glucose (Gibco/BRL); 5% fetal bovine serum (HyClone); MEM non-essential amino acids (1%) (Gibco/BRL); hypoxanthine/thymidine (1%) (Gibco/BRL); and glutamine/penicillin/streptomycin (1%) (Irvine Scientific).

Selective medium contained: DMEM (high glucose); 5% dialyzed fetal bovine serum (HyClone); MEM non-essential amino acids; and glutamine/penicillin/streptomycin.

2× HEPES-buffered saline (HBS) contained: 280 mM NaCl; 10 mM KCl; 1.5 mM $Na_2HPO_4$; 12 mM dextrose; and 50 mM HEPES.

Tris-buffered saline plus Tween (TBST) contained: 137 mM NaCl; 20 mM Tris/HCl pH 7.5; and 0.1% Tween-20.

Methods

Transfection and Selection

CHOd⁻ cells (passage 20) were seeded into 60 mm tissue culture dishes (Falcon) at a density of $8\times10^5$ cells per dish in CHOd⁻ growth medium. On the following day, about three hours prior to transfection, the medium on the cells was replaced with fresh medium.

Plasmid constructs containing the appropriate GONE cONA were prepared using well known techniques. Eor example, the plasmid construct pDSRα2 was prepared substantially in accordance with the process described in the co-owned and copending U.S. patent application Ser. No. 07/501,904 filed Mar. 29, 1990. now abandoned, (also see, European Patent Application No. 90305433, granted Sept. 2, 1998, EP Patent No. 0398753 and WO 90/14363 (1990), the disclosures of which are hereby incorporated by reference. An exemplary plasmid map which illustrates the structural organization of the vector is depicted in FIG. 2. It will be appreciated by those skilled in the art that a variety of nucleic acid sequences encoding the mature GDNF protein, such as the sequences depicted in FIGS. 1, 3 and 4, may also be used.

A HindIII-XbaI DNA fragment containing the human GDNF coding sequences and the consensus Kozak sequences, CCACC(ATG) was retrieved by restriction enzyme digestion from a pcDNA3 based expression vector (Invitrogen, San Diego, Calif.). The DNA fragment was directly cloned into HindIII/XbaI cut pDSRα2. The resulting plasmid was called pSW5. The plasmid DNA of pSW5 was linearized at the PuvI site prior to transfection.

pDSRα2 (FIG. 2) is a derivative of the plasmid pCD (Okayama & Berg, *Mol. Cell Biol.* 3: 280-289, 1983) with three main modifications: (i) the SV40 polyadenylation signal has been replaced with the signal from the α-subunit of bovine follicular stimulating hormone, α-bFSH (Goodwin et al., *Nucleic Acids Res.* 11: 6873-6882, 1983); (ii) a mouse dihydrofolate reductase minigene (Gasser et al., *Proc. Natl. Acad. Sci.* 79: 6522-6526, 1982) has been inserted downstream from the expression cassette to allow selection and amplification of the transformants; and (iii) a 267 bp fragment containing the "R-element" and part of the "U5" sequences of the long terminal repeat (LTR) of human T-cell leukemia virus type I (HTLV-I) has been cloned and inserted between the SV40 promoter and the splice signals as described previously (Takebe et al., *Mol. Cell Biol.* 8: 466-472, 1988).

Solutions of DNA were prepared containing a final concentration of 3.0 μg/dish GDNF-plasmid DNA, 7.0 μg/dish mouse kidney genomic carrier DNA (Clontech), 25 μl/dish 2.5M $CaCl_2$, and sterile distilled water to a final volume of 250 μl/dish. DNA solutions containing pDSRα2 vector DNA or carrier DNA alone were similarly prepared as positive and negative controls, respectively. The DNA solutions were added dropwise to an equal volume of 2× HEPES-buffered saline while passing air bubbles through the solution. The DNA/HBS solutions were incubated at room temperature for 30 minutes.

The medium was removed from the CHOd⁻ cell cultures, and 500 μl of the DNA solutions were added per dish. The dishes were incubated at room temperature for 30 minutes, after which time CHOd⁻ medium (5.0 ml.) was added to each dish. The dishes were then incubated at 37° C. overnight.

On the following day the medium was replaced with fresh CHOd⁻ medium. The next day, when the cells had reached confluence, the cultures were trypsinized and replated in 100 mm dishes (Falcon) at a ratio of 1×60 mm dish to 8×100 mm dishes. Cells were replated in selective medium. The cultures were re-fed with fresh medium every two to three days.

After 15 days, colonies of transfected cells were isolated using glass cloning cylinders, trypsinized, and replated into 24-well dishes (Falcon). A total of 40 colonies was isolated from the GDNF/pSW5-transfected cells. The remaining cells on the dishes were trypsinized, pooled, and replated into two 100 mm dishes (one pool for each DNA construct).

Screening of Transfected Cells:

The 24-well and pool cultures were grown to confluence, at which time the growth medium was removed and replaced with serum-free medium (400 μl/well or 4 ml/dish). Cells were incubated for 48 hours, and the conditioned medium was harvested. The conditioned medium samples were analyzed for GDNF protein expression by western blot. Aliquots of conditioned medium (20 μl or 40 μl) were diluted with electrophoresis sample buffer (with or without β-mercaptoethanol). Samples containing β-mercaptoethanol were boiled for three minutes (reducing conditions). Both reduced and non-reduced samples were run on 16% Tris-glycine gels (Novex). Gels were electroblotted onto nitrocellulose filters (Schleicher and Schuell BA-83, 0.2μ). The blots were rinsed with TBST and then incubated in a blocking solution of 5% dried milk (Carnation) in TBST for 30 minutes at room temperature. Blots were then treated with GDNF antiserum (rabbit polyclonal antisera raised against *E. coli*-derived GDNF; 1:1000 in 5% milk/TBST) for one hour at room temperature. The blots were then rinsed with TBST and washed 1×10 minutes and 2×5 minutes with 1% milk/TBST. They were then treated with anti-rabbit Ig-horse radish peroxidase-conjugated secondary antibody (1:15,000 in 1% milk/TBST) for 20 minutes. Blots were rinsed and washed with TBST 1×20 minutes and 2×10 minutes, followed by treatment with ECL reagents (Amersham) for one minute and exposure to Hyperfilm-ECL (Amersham).

The following process describes the purification of CHO-expressed GDNF and a CHO-derived clipped GDNF homodimer, from one liter of conditioned media. Because of significant protease action in the CHO medium, clipping the chain at residue 31, the procedure may include the use of a protease inhibitor during purification.

Step 1. Bead Chromatography:

Serum free conditioned media was made 20 mM 2-[N-Morpholino] ethane sulfonate (MES), pH 6.0, by adding one fiftieth volume of 1 M MES, pH 6.0. Twenty five milliliters of SP Sepharose Big Bead resin (Pharmacia), equilibrated with 20 mM MES, pH 6.0, was added and stirred at 4° C. for one hour. The resin was collected by allowing it to settle and decanting off the conditioned media. The decanted media was filtered through a fritted disc filter to recover any unsettled resin. The settled resin and that recovered by filtration was resuspended and poured into a 2.5 cm diameter column and washed with three column volumes of 0.15 M NaCl, 20 mM MES, pH 6.0 (A buffer). Protein was eluted with a 300 ml gradient from A buffer to 1.0 M NaCl, 20 mM MES, pH 6.0 (B buffer), at a flow rate of 0.2 column volumes/minute with absorbance monitored at 280 nm. Fractions containing 1.1 column volumes were collected. The presence of GDNF in the fractions was detected by Western blotting analysis. Fractions containing GDNF were pooled for further purification. GDNF eluted between 0.3 and 0.6 M NaCl.

Step 2. HPLC C4 Chromatography:

The pool from Step 1 was made 0.1% (v/v) trifluoroacetic acid (TFA), vacuum filtered through a 0.45 micron filter, and applied to a Vydac C4 column (0.46×25 cm) conditioned with aqueous 10% acetonitrile, 0.1% TFA (A buffer). Protein was eluted with a 2%/minute linear gradient over 50 minutes from A buffer to aqueous 90% acetonitrile, 0.1% TFA (B buffer) with absorbance measured at 280 nm. One milliliter fractions were collected, and the presence of GDNF was detected by Western blotting analysis. GDNF was eluted between 45% and 55% acetonitrile. Fractions were taken to dryness in vacuum.

Step 3. High Performance S Chromatography:

Fractions containing GDNF from Step 2 were resolublized in one milliliter of 0.15 M NaCl, 10 mM Tris, pH 8.0, and applied to a 0.75×7.5 cm TSK-Gel 5WP high performance S column (Toso Haas). A linear gradient of 0.4%/minute was run from 0.15 M NaCl, 10 mM Tris, pH 8.0 (A buffer) to 1.0 M NaCl, 10 mM Tris, pH 8.0 (B buffer) over 50 minutes at a flow rate of 1 ml/min. One minute fractions were collected with absorbance measured at 280 nm. At 35% B buffer, the gradient was changed to 6.5%/minute over 10 minutes. Western blot analysis of the fractions showed four major GDNF components. Three of the components eluted during the 0.4%/minute gradient and the fourth was eluted during the 6.5%/minute gradient. Appropriate pools were made of similar components and submitted for sequencing. Sequencing analyses identified an approximately 29-36 kD pool as [$Arg^{32}$-$Ile^{134}$] truncated GDNF protein. The component at approximately 38-40 kD was identified as an [$Arg^{32}$-$Ile^{134}$] truncated GDNF/mature GDNF heterodimer. Finally, the approximately 41-44 kD component which was isolated during the latter portion of the gradient was identified by sequencing as the mature GDNF homodimer.

Example 2

Mature Human GDNF Produced in *E. coli*

The bacterial expression of mature human GDNF may be achieved in accordance with the process described in Lin et al. (U.S. patent application Ser. No. 08/182,183 filed May 23, 1994 and its parent applications; PCT/US92/07888 filed Sep. 17, 1992 (WO 93/06116); and European Patent Application No. 92921022.7 (Publication No. EP 610 254); the disclosures of which are hereby incorporated by reference. Based upon the description of the present invention, those of ordinary skill in the art will appreciate that a variety of materials and methods may readily be used or adapted for suitable expression in *E. coli* and other bacteria. For example, alternate polynucleotides, such as those depicted in FIGS. 1, 3 and 4, may be used in the expression process.

Refolding and Purification of Expressed Mature GDNF

The transformed cells were processed at 5° C. (unless otherwise noted) as follows: cell paste (30 gm) was suspended into a final volume of 200 milliliters using 25 mM Tris, pH 8.5 containing 5 mM EDTA, to yield a final cell slurry of 15% (w/v). The cells were thoroughly dispersed using a Biospec hand-held low shear homogenizer. The slurry was passed twice through a microfluidizer at 14,500 psi to break the cells and release inclusion bodies. The resulting homogenate was then centrifuged for 30 minutes at 16,000× g. The pellet of inclusion bodies resulting from the centrifugation was washed by resuspension in chilled water to a final volume of 240 milliliters using the Biospec homogenizer, as before, to form a slurry. A sample of this slurry was kept for HPLC analysis of the GDNF expression level. The remaining slurry was centrifuged for 30 minutes at 16,000×g. The supernatant was discarded, and a small amount of cold water was added to the centrifuge bottle and gently swirled to remove the loosely formed membrane layer on top of the inclusion bodies pellet. The pellet was resuspended with the Biospec homogenizer using a sufficient volume of cold water to yield a concentration of 2 mg/ml of GDNF. The inclusion bodies were then solubilized by mixing the final inclusion bodies suspension (25 ml) and 8M guanidine HCl (25 ml) containing 180 mM cysteine HCl, and 50 mM Tris HCl, pH 8.7. The solubilization mixture was stirred at 25° C. for 60 to 90 minutes after which it was poured, with mixing, into 2 M urea (450 ml, at 5° C.) containing 20 mM Tris HCl, pH 8.75 and 0.2 M guanidine HCl. This refold mixture was slowly stirred at 5° C. for 72 hours.

The refolded GDNF was partially purified as follows: 20 mM sodium acetate buffer (250 ml, pH 5) at 5° C. was added with rapid stirring to the refold mixture, and the pH was adjusted to 5 with glacial acetic acid. The resulting precipitate was removed by centrifugation at 13,600×g for 45 minutes at 5° C. The supernatant from this centrifugation was used as the load solution for the next purification step involving cation exchange chromatography with SP-big bead resin (Pharmacia). The column was operated at 5° C. using 20 mM sodium acetate (pH 5) as the equilibration, rinsing, and elution buffer system. A bed of resin (5 ml) was sanitized with 5 column volumes (CV) of 0.2N NaOH and then equilibrated with the acetate buffer (5 CV). The load solution (190 ml) was applied to the column at 0.5 CV/minute followed by a 10 CV rinse with acetate buffer at the same flow rate. The GDNF was then eluted off the resin with a 20 CV linear gradient of NaCl from 0.3 M to 0.9M in the acetate buffer at a flow rate of 0.1 CV/minute. The column eluate was monitored by absorbance at 280 nm and collected as fractions which were assayed by SDS-PAGE. The fractions containing GDNF were pooled from the front of the GDNF peak at 10% peak height through to the back of the peak to 10% peak height. The protein in this pool was entirely GDNF and, depending upon the production strain used, contained 32% to 12% contamination as modified GDNF forms. The pool was then dialyzed against PBS or other formulation buffers and, in some cases, concentrated by ultrafiltration to 25 mg/ml. Both wild type and analogue forms of GDNF purified by this procedure were characterized by reverse phase HPLC, cation exchange HPLC, mass spectrometry, and endotoxin levels in order to compare purities of the preparations in relation to the corresponding production strains.

Example 3

Recombinant Production of Truncated GDNF in *E. coli*

Exemplary truncated GDNF proteins were produced substantially in accordance with the techniques described in Lin et al. (U.S. patent application Ser. No. 08/182,183 filed May 23, 1994, supra). Alternative bacterial expression materials and methods, as described above, may also be used. The *E. coli*-expressed truncated GDNF proteins included the [$Pro^{23}$-$Ile^{134}$], [$Arg^{32}$-$Ile^{134}$], and [$Gly^{33}$-$Ile^{134}$] truncated GDNF proteins as depicted in FIGS. 5, 6 and 7, respectively. The polynucleotides encoding these exemplary truncated GDNF proteins were constructed as depicted in FIGS. 5, 6 and 7, but corresponding polynucleotides such as those depicted in FIGS. 1, 3 and 4 may also be used. The polynucleotides were constructed by standard PCR procedures as described in *PCR Technology, Principles and Applications for DNA Amplification*, Henry A. Erlich, ed., Stockton Press, N.Y., 1989 (Chapter 6, Using PCR to Engineer DNA) the disclosure of which is hereby incorporated by reference.

Example 4

Bioassay for Dopaminergic Neuron Neurotrophic Activity

The *E. coli*-expressed [$Pro^{23}$-$Ile^{134}$], [$Arg^{32}$-$Ile^{134}$], [$Gly^{33}$-$Ile^{134}$] and [$Lys^{37}$-$Ile^{134}$] truncated GDNF proteins of Example 3 and the CHO-derived [$Arg^{32}$-$Ile^{134}$] truncated GDNF protein of Example 1 were assessed on a qualitative basis for their ability to promote dopamine uptake by *substantia nigra* dopaminergic neurons.

Materials

The following materials are used in an assay to assess the survival of dopaminergic neurons in the presence of truncated GDNF proteins:

Cell Culture Media

High glucose Dulbecco's Modified Eagle's Medium (DMEM; catalog #11965-092), Ham's F12 medium (F12; #11765-021), Leibovitz's L15 medium without sodium bicarbonate (#41300-039), B27 medium supplement (#17504-010), penicillin/streptomycin (#15070-014), L-glutamine (#25030-016), Dulbecco's phosphate-buffered saline (D-PBS; #14190-052), Hank's balanced salt solution with calcium and magnesium salts (HBSS; #24020-026), N-2-hydroxyethylpiperazine-N'-2-ethanesulfonic acid (HEPES; #15630-015), mouse laminin (#23017-015), and bovine serum albumin fraction V (#110-18-017) were all from GIBCO, Grand Island, N.Y. Heat-inactivated horse serum was from HyClone, Logan, Utah. Conalbumin (C-7786), poly-L-ornithine hydrobromide (P-3655), bovine insulin (I-5500), human transferrin (T-2252), putrescine (P-6024), progesterone (P-6149), sodium selenite (S-9133), metrizamide (M-3383) were all from Sigma Chemical Company, Saint-Louis, Mo. Papain, deoxyribonuclease I (DNAase) and ovalbumin (Papain dissociation system) were from Worthington Biochemicals, Freehold, N.J.

Falcon sterile 96-well microplates (#3072), tissue culture plastic ware and polypropylene centrifuge tubes were from Becton-Dickinson, Oxnard, Calif. Nunc Lab-Tek tissue culture chamber coverglasses (#136439) were from Baxter, Irvine, Calif; 20 μm (#460) nylon mesh was from Tetko, Elmsford, N.Y.; and 4" dissecting forceps and 4" dissecting scissors were from Roboz Surgical, Washington, D.C.

Antibodies and Related Reagents

Polyclonal rabbit anti-tyrosine hydroxylase antibodies (TE101) were from Eugene Tech, Ridgefield Park, N.J.; polyclonal rabbit anti-neuronal-specific enolase antibodies (NSE, AB951) were from Chemicon, Temecula, Calif.; and biotinylated goat anti-rabbit IgG and peroxidase-conjugated avidin/biotin complex (ABC Elite; Vectastain kit PK-6100) were from Vector Laboratories, Burlingame, Calif. 3',3'-diaminobenzidine was from Cappel Laboratories, West Chester, Pa. Superblock blocking buffer in PBS (#37515) was from Pierce Chemical Company, Rockford, Ill. Triton X-100 (X100), Nonidet P-40 (N6507) and hydrogen peroxide (30%, v/v; H1009) were from Sigma. GBR-12909 dopamine uptake inhibitor (D-052) was from RBI, Natick, Mass. $^3$H-dopamine (tritiated dopamine, NE-131; 21 Ci/mmol) was from New England Nuclear, Boston, Mass. Optiphase Supermix scintillation cocktail was from Wallac, Turku, Finland. White ViewPlate-96 microplates (#6005182) were from Packard Instruments Corporation, Meriden, Conn. All other reagents were obtained from Sigma Chemical Company, unless otherwise specified.

Preparation of Media

The basal medium was prepared as a 1:1 mixture of DMEM and F12 medium, and was supplemented with B27 medium supplement added as a 50-fold concentrated stock solution. L-glutamine was added at a final concentration of about 2 mM, penicillin at about 100 IU/l, and streptomycin at about 100 mg/l. Heat-inactivated horse serum was added to a final concentration of about 15 percent. After mixing, the pH was adjusted to about 7.3, and the media were kept at 4° C. The media were prepared fresh just before use in order to minimize inter-experimental variations. Plastic pipettes and containers were used throughout to minimize protein adsorption.

Culture Substratum

To encourage optimal attachment of substratum neurons and neurite outgrowth, microtiter plate surfaces (the culture substratum) were modified by sequential coatings with poly-L-ornithine and laminin, as follows. The plate surfaces were completely covered with a 0.1 mg/ml sterile solution of poly-L-ornithine in 0.1 M boric acid (pH 8.4) for at least one hour at room temperature, followed by a sterile wash with Super-Q water. The water wash was then aspirated, and a 1.0 μg/ml solution of mouse laminin in PBS was added and incubated at 37° C. for two hours. These procedures were conducted just before using the plates in order to ensure reproducibility of the results.

Preparation of Embryonic Rat Substantia Nigra Cultures

Embryonic rat brains were used as the source of *substantia nigra* dopaminergic neurons. Timed-pregnant Sprague-Dawley rats at embryonic day 15 were used. A maximum of 36 embryos (about three litters) were processed per experiment. The pregnant rats were killed by exposure to $CO_2$, their abdominal cavities opened with dissecting scissors, and the fetuses were removed from the uteri. Fetal brains were then dissected and cleaned of blood and meninges, and the ventral tegmental area containing the *substantia nigra* was dissected using well-defined anatomical landmarks (Altman and Bayer, *Atlas of Prenatal Rat Brain Development*, CRC Press, Boca Raton, Fla., 1995). The tissues were collected in ice-cold D-PBS, transferred into 10 milliliters of dissociation medium (120 units papain and 2000 units DNAase in HBSS) and then incubated for 45 minutes at about 37° C. on a rotary platform shaker at about 200 rpm. The cells were then dispersed by trituration through fire-polished Pasteur pipettes, sieved through a 20 μm Nitex mesh to discard undissociated tissue, and centrifuged for five minutes at 200×g using an IEC clinical centrifuge. The resulting cell pellet was resuspended into HBSS containing ovalbumin and about 500 units DNAase, layered on top of a 4% ovalbumin solution (in HBSS) and centrifuged for about 10 minutes at 500×g. The final pellet was resuspended in complete culture medium (see above), adjusted to about 28,000 cells/ml, and seeded in aliquots (90 μl) into the 6 mm-wells of the 96-well microplates previously coated with polyornithine and laminin. Attachment of cells occurred rapidly, and the plating efficiency was about 75 percent.

Immunohistochemistry of Dopaminergic Neurons

An indirect immunoperoxidase method described by Louis et al. (*J. Pharmacol. Exp. Therap.*, 262:1274-1283, 1992;

*Science*, 259:689-692,1993) was used with slight modifications, as follows, to characterize the dopaminergic neurons in cultures of *substantia nigra*. Cultures were fixed for about 30 minutes at room temperature with 4% paraformaldehyde in D-PBS, pH 7.4, followed by three washes in D-PBS (200 µl per 6-mm well). The fixed cultures were then incubated in Superblock blocking buffer in PBS, containing 1% NP-40 to increase the penetration of the antibodies. The primary rabbit anti-tyrosine hydroxylase antibodies were then applied at a dilution of about 1:2000 in the same buffer and incubated for one hour at 37° C. on a rotary shaker. After three washes with D-PBS, the bound antibodies were detected using goat-anti-rabbit biotinylated IgG at about a 1:500 dilution; these secondary antibodies were incubated with the cells for about one hour at 37° C. The cells were then washed three times with D-PBS, and the secondary antibodies were detected with avidin-biotin-peroxidase complex diluted at 1:500, and the cells were incubated for about 45 minutes at 37° C. After three more washes with D-PBS, the cultures were reacted for 5-20 minutes in a solution of 0.1 M Tris-HCl, pH 7.4, containing 0.04% 3',3'-diaminobenzidine-(HCl)4, 0.06 percent $NiCl_2$ and 0.02 percent hydrogen peroxide.

Determining Neuronal Survival

Substantia nigra cultures were fixed and processed for immunostaining as described above, and then examined with bright-light optics at 200× magnification. The number of neurons stained for tyrosine hydroxylase was counted in the entire 6-mm well of the 96-well microplates Viable neurons were characterized as having a regularly-shaped cell body, with a major axon-like process and several dendrite-like processes. Neurons showing signs of degeneration, such as having irregular, vacuolated perikarya or fragmented neurites, were excluded from the counts (most of the degenerating neurons, however, detached from the culture substratum). Dopaminergic neuron cell numbers were expressed either as TH-positive neurons/6-mm well or as the fold-change relative to control dopaminergic neuron density.

Determining Dopamine Uptake

Dopamine uptake was determined in cultures of 15-day-old embryonic rat *substantia nigra* neurons that had been established in white ViewPlate-96 microplates. The cultures were washed with pre-warmed uptake buffer (about 100 µl) which consists of a modified Krebs-Ringer solution, pH 7.4, containing about 120 mM NaCl, 4,7 mM KCl, 1.8 mM $CaCl_2$, 1.2 mM $MgSO_4$, 32 mM $NaHPO_4$, 1.3 mM EDTA, and 5.6 mM D-glucose. The uptake buffer also contained 1 mM ascorbic acid and 50 µM pargyline to prevent the oxidation of dopamine. The cells were then preincubated at 37° C. for about 10 minutes in uptake buffer. Tritiated dopamine ($^3$H-DA, 21 Ci/mmol) was then added to the *substantia nigra* cultures at a concentration of about 50 nM in 75 µl of uptake buffer, and the cultures were incubated for about 60 minutes at 37° C. Non-specific dopamine uptake was determined by incubating the cultures with uptake buffer containing the dopamine uptake inhibitor GBR-12909 (1 µM). Non-specific uptake represented less than about one percent of total uptake. The uptake assays were arrested by aspiration of the incubation medium followed by three rapid washes with ice-cold uptake buffer (about 120 µl). The cells were then lysed by addition of Optiphase Supermix scintillation cocktail (200 µl), and radioactivity was determined by scintillation spectrometry using a Wallac MicrobetaPlus 96-well microplate counter (i.e., dopamine uptake is analyzed by scintillation counting of the retained tritium in the cultures). The results are expressed either as dpm/6-mm well or as the fold-change relative to control cultures.

Assays

Dopaminergic Neuron Survival and Morphological Development

Cultures of embryonic day 15 (E15) rat *substantia nigra* enriched in dopaminergic neurons were used to demonstrate the effect of truncated GDNF proteins on the survival of dopaminergic neurons. The cultures were grown in polyornithine-and laminin-coated 96-well microplates for up to six days alone or in the presence of various concentrations (ranging from about 1 pg/ml to about 10 ng/ml) of the following proteins: *E. coli*-expressed mature hGDNF; *E. coil*-expressed [$Pro^{23}$-$Ile^{134}$], [$Arg^{32}$-$Ile^{134}$], [$Gly^{33}$-$Ile^{134}$] and [$Lys^{37}$-$Ile^{134}$] truncated GDNF proteins; CHO cell-expressed mature hGDNF; and CHO cell-derived [$Arg^{32}$-$Ile^{134}$] truncated GDNF protein. The culture medium consisted of DMEM/F12 supplemented with 15% heat-inactivated horse serum (E15 cultures) or 2.5% heat-inactivated horse serum, D-glucose, HEPES, insulin and transferrin (P6 cultures). Immunostaining for tyrosine hydroxylase (TH), the rate-limiting enzyme in dopamine biosynthesis, was used as a marker for dopaminergic neurons. Since noradrenergic neurons in the rhombencephalon also stain positive for TH, great care was taken to dissect an area restricted to the ventral tegmentum of the mesencephalon and to avoid the more caudal regions containing the noradrenergic cell bodies. After six days, the E15 cultures typically consisted of about 70% neurons as identified by neuronal specific enolase immunostaining (described above) and 30% non-neuronal cells (which had a flattened, phase-dark appearance); dopaminergic neurons represented about 10-15% of the neuron population.

After six days, the cultures were fixed with paraformaldehyde and immunostained for tyrosine hydroxylase, a marker that identifies dopaminergic neurons in these cultures. All the tyrosine-hydroxylase-positive neurons present in a 6-mm well were counted under brightfield optics. Three to six different wells were analyzed for each experimental condition. The results were expressed as the percentages of the number of tyrosine-hydroxylase-positive neurons found in control cultures.

Cultures of E15 *substantia nigra* treated with 1.0 ng/ml of GDNF, CHO cell-expressed GDNF or *E. coli*-expressed GDNF, contained about 38% and 27% more TH-immunoreactive neurons, respectively, than untreated control cultures, indicating that both GDNF species promote the survival of dopaminergic neurons. Cultures of E15 *substantia nigra* treated with 1.0 ng/ml of truncated GDNF protein showed a similar increase in the number of TH-positive neurons in cultures after six days in vitro: 42% for CHO cell-derived [$Arg^{32}$-$Ile^{134}$] truncated GDNF protein; and 26% and 17% for *E. coli*-expressed [$Arg^{32}$-$Ile^{134}$] and [$Gly^{33}$-$Ile^{134}$] truncated GDNF proteins, respectively.

Comparison of control cultures and cultures treated with mature and truncated GDNF proteins also revealed pronounced effects of all the GDNF proteins on the morphological differentiation of dopaminergic neurons. The effects of the [$Arg^{32}$-$Ile^{134}$] and [$Gly^{33}$-$Ile^{134}$] truncated GDNF proteins were identical to their respective mature GDNF protein counterparts. TH-immunoreactive neurons in all GDNF-treated cultures possessed significantly more complex and extensive neuritic arborization, as well as a higher degree of neurite branching and an overall larger soma size, than did TH-positive neurons in control cultures.

Dopamine Uptake

Dopamine uptake measures the number and activity of high affinity dopamine reuptake transporter sites and reflects the functional differentiation of dopaminergic neurons.

Dopamine uptake was measured in cultures of E15 rat *substantia nigra* after six days in vitro either with or without mature GDNF or truncated GDNF proteins. In these cultures, dopamine uptake had the pharmacological profile characteristic of dopaminergic neurons, i.e., it was nearly completely blocked (more than 98 percent) by 1.0 µM GBR-12909, a dopamine transporter inhibitor specific for dopaminergic neurons (ID50=20 nM). This indicates that dopamine uptake measurements do not reflect the presence of contaminating noradrenergic neurons, which can take up dopamine through norepinephrine transporters but are not sensitive to GBR-12909 inhibition. The effects of CHO-cell-expressed mature GDNF and the CHO-derived [$Arg^{32}$-$Ile^{134}$] truncated GDNF protein were identical: about 65% increase, with an ED50 of about 20 pg/ml. *E. coli*-expressed [$Pro^{23}$-$Lys^{37}\Delta Asn^{37}$-$Ile^{134}$] truncated GDNF protein, as depicted in FIG. 5, demonstrated a 65% increase, with an ED50 of about 40 pg/ml.

The effects on dopamine uptake of the *E. coli*-expressed mature protein and the *E. coli*-expressed [$Arg^{32}$-$Ile^{134}$], [$Gly^{33}$-$Ile^{134}$] and [$Lys^{37}$-$Ile^{134}$] truncated GDNF proteins were the same: about 50% increases, with ED50s of about 50 pg/ml.

These results indicate that the truncated GDNF proteins act as potent survival-promoting and differentiation-inducing factors for *substantia nigra* dopaminergic neurons. As such, they are envisioned to be particularly useful in the treatment of Parkinson's disease, a neurological disorder characterized by decreased emotional acuity, slowing of both voluntary and involuntary muscle movement, muscular rigidity, and tremor. Such symptoms are attributed to the progressive degeneration of dopamine-producing neurons located in the *substantia nigra*. Degeneration of these neurons ("dopaminergic neurons") results in a decrease of dopamine in an adjacent region of the brain called the striatum.

What is claimed is:

1. A method for promoting the survival or function of dopaminergic neurons comprising administering to a patient a pharmaceutical composition comprising:
   (a) a pharmaceutically acceptable vehicle, and
   (b) a truncated glial cell line-derived neurotrophic factor (GDNF) protein product consisting of the amino acid sequence
   $Cys^{41}$ through $Cys^{133}$ of SEQ ID NO:2.

2. A method for promoting the survival or function of dopaminergic neurons comprising administering a pharmaceutical composition comprising:

(a) a pharmaceutically acceptable vehicle, and
   (b) a truncated GDNF protein product consisting of the formula: $X\text{-}(Cys^{41}\text{-}Cys^{133})\text{-}Y$, wherein
   $Cys^{41}$ through $Cys^{133}$ is SEQ ID NO:2
   Y is absent or a carboxy-terminus amino acid residue of $Ile^{134}$, and
   X is a methionylated or nonmethionylated amine group of $Cys^{41}$ or amino-terminus amino acid residue(s) selected from the group consisting of:

|  |  |
   |---|---|
   | G | |
   | RG | |
   | NRG | |
   | KNRG | (SEQ ID NO:3) |
   | GKNRG | (SEQ ID NO:4) |
   | RGKNRG | (SEQ ID NO:5) |
   | QRGKNRG | (SEQ ID NO:6) |
   | GQRGKNRG | (SEQ ID NO:7) |
   | RGQRGKNRG | (SEQ ID NO:8) |
   | RRGQRGKNRG | (SEQ ID NO:9) |
   | G RRGQRGKNRG | (SEQ ID NO:10) |
   | KG RRGQRGKNRG | (SEQ ID NO:11) |
   | GKG RRGQRGKNRG | (SEQ ID NO:12) |
   | RGKG RRGQRGKNRG | (SEQ ID NO:13) |

-continued

```
    SRGKG RRGQRGKNRG  (SEQ ID NO:14)
   NSRGKG RRGQRGKNRG  (SEQ ID NO:15)
  ENSRGKG RRGQRGKNRG  (SEQ ID NO:16)
 PENSRGKG RRGQRGKNRG  (SEQ ID NO:17)
NPENSRGKG RRGQRGKNRG  (SEQ ID NO:18)
ANPENSRGKG RRGQRGKNRG (SEQ ID NO:19)
       A ANPENSRGKG RRGQRGKNRG  (SEQ ID NO:20)
      AA ANPENSRGKG RRGQRGKNRG  (SEQ ID NO:21)
     AAA ANPENSRGKG RRGQRGKNRG  (SEQ ID NO:22)
    QAAA ANPENSRGKG RRGQRGKNRG  (SEQ ID NO:23)
   RQAAA ANPENSRGKG RRGQRGKNRG  (SEQ ID NO:24)
  NRQAAA ANPENSRGKG RRGQRGKNRG  (SEQ ID NO:25)
 RNRQAAA ANPENSRGKG RRGQRGKNRG  (SEQ ID NO:26)
ERNRQAAA ANPENSRGKG RRGQRGKNRG  (SEQ ID NO:27)
RERNRQAAA ANPENSRGKG RRGQRGKNRG (SEQ ID NO:28)
RRERNRQAAA ANPENSRGKG RRGQRGKNRG (SEQ ID NO:29)
 P RRERNRQAAA ANPENSRGKG RRGQRGKNRG (SEQ ID NO:30)
LP RRERNRQAAA ANPENSRGKG RRGQRGKNRG (SEQ ID NO:31)
VLP RRERNRQAAA ANPENSRGKG RRGQRGKNRG (SEQ ID NO:32)
AVLP RRERNRQAAA ANPENSRGKG RRGQRGKNRG (SEQ ID NO:33)
MAVLP RRERNRQAAA ANPENSRGKG RRGQRGKNRG (SEQ ID NO:34)
QMAVLP RRERNRQAAA ANPENSRGKG RRGQRGKNRG (SEQ ID NO:35)
KQMAVLP RRERNRQAAA ANPENSRGKG RRGQRGKNRG (SEQ ID NO:36)
DKQMAVLP RRERNRQAAA ANPENSRGKG RRGQRGKNRG (SEQ ID NO:37)
and
PDKQMAVLP RRERNRQAAA ANPENSRGKG RRGQRGKNRG (SEQ ID NO:38)
```

3. The method according to claim 2 wherein X is SEQ ID NO: 3.

4. The method according to claim 2 wherein X is SEQ ID NO: 7.

5. The method according to claim 2 wherein X is SEQ ID NO: 8.

6. The method according to claim 2 wherein X is SEQ ID NO: 14.

7. The method according to claim 2 wherein X is SEQ ID NO: 17.

8. The method according to claim 2 wherein X is SEQ ID NO: 51.

9. The method according to claim 2 wherein X is SEQ ID NO: 18.

10. The method according to claim 2 wherein X is SEQ ID NO: 24.

11. The method according to 2 wherein X is G, RG, or NRG.

12. A method for promoting the survival or function of dopaminergic neurons comprising administering to a patient a pharmaceutical composition comprising:

(a) a pharmaceutically acceptable vehicle, and (b) a truncated GDNF protein product consisting of the amino acid sequence of SEQ ID NO:42.

13. A method for promoting the survival or function of dopaminergic neurons comprising administering to a patient a pharmaceutical composition comprising:

(a) a pharmaceutically acceptable vehicle, and (b) a truncated GDNF protein product consisting of the amino acid sequence of SEQ ID NO:44.

14. A method for promoting the survival or function of dopaminergic neurons comprising administering to a patient a pharmaceutical composition comprising:

(a) a pharmaceutically acceptable vehicle, and (b) a truncated GDNF protein product consisting of the amino acid sequence of SEQ ID NO:46.

15. The method according to claim 1 wherein said truncated GDNF protein product is glycosylated.

16. The method according to any of claims 2-14 wherein said truncated GDNF protein product is glycosylated.

17. The method according to claim 1 wherein said truncated GDNF protein product is conjugated to a water soluble polymer.

18. The method according to any of claims 2-14 wherein said truncated GDNF protein product is conjugated to a water soluble polymer.

19. The method according to claim 17 wherein said water soluble polymer is PEG.

20. The method according to claim 18 wherein said water soluble polymer is PEG.

* * * * *

SEQUENCE LISTING

```
<160> NUMBER OF SEQ ID NOS: 51

<210> SEQ ID NO 1
<211> LENGTH: 402
<212> TYPE: DNA
<213> ORGANISM: Homo sapiens
<220> FEATURE:
<221> NAME/KEY: CDS
<222> LOCATION: (1)..(402)

<400> SEQUENCE: 1 tca cca gat aaa caa atg gca gtg ctt cct aga aga gag cgg aat cgg      48
Ser Pro Asp Lys Gln Met Ala Val Leu Pro Arg Arg Glu Arg Asn Arg
1               5                  10                  15 cag gct gca gct gcc aac cca gag aat tcc aga gga aaa ggt cgg aga      96
Gln Ala Ala Ala Ala Asn Pro Glu Asn Ser Arg Gly Lys Gly Arg Arg
            20                  25                  30 ggc cag agg ggc aaa aac cgg ggt tgt gtc tta act gca ata cat tta     144
Gly Gln Arg Gly Lys Asn Arg Gly Cys Val Leu Thr Ala Ile His Leu
        35                  40                  45 aat gtc act gac ttg ggt ctg ggc tat gaa acc aag gag gaa ctg att     192
Asn Val Thr Asp Leu Gly Leu Gly Tyr Glu Thr Lys Glu Glu Leu Ile
    50                  55                  60 ttt agg tac tgc agc ggc tct tgc gat gca gct gag aca acg tac gac     240
Phe Arg Tyr Cys Ser Gly Ser Cys Asp Ala Ala Glu Thr Thr Tyr Asp
65                  70                  75                  80 aaa ata ttg aaa aac tta tcc aga aat aga agg ctg gtg act gac aaa     288
Lys Ile Leu Lys Asn Leu Ser Arg Asn Arg Arg Leu Val Thr Asp Lys
                85                  90                  95 gta ggg cag gca tgt tgc aga ccc atc gcc ttt gat gat gac ctg tcg     336
Val Gly Gln Ala Cys Cys Arg Pro Ile Ala Phe Asp Asp Asp Leu Ser
            100                 105                 110 ttt tta gat gat aac ctg gtt tac cat att cta aga aag cat tcc gct     384
Phe Leu Asp Asp Asn Leu Val Tyr His Ile Leu Arg Lys His Ser Ala
        115                 120                 125 aaa agg tgt gga tgt atc                                             402
Lys Arg Cys Gly Cys Ile
    130

<210> SEQ ID NO 2
<211> LENGTH: 134
<212> TYPE: PRT
<213> ORGANISM: Homo sapiens
```

```
<400> SEQUENCE: 2

Ser Pro Asp Lys Gln Met Ala Val Leu Pro Arg Arg Glu Arg Asn Arg
1               5                   10                  15

Gln Ala Ala Ala Asn Pro Glu Asn Ser Arg Gly Lys Gly Arg Arg
            20                  25                  30

Gly Gln Arg Gly Lys Asn Arg Gly Cys Val Leu Thr Ala Ile His Leu
            35                  40                  45

Asn Val Thr Asp Leu Gly Leu Gly Tyr Glu Thr Lys Glu Glu Leu Ile
            50                  55                  60

Phe Arg Tyr Cys Ser Gly Ser Cys Asp Ala Ala Glu Thr Thr Tyr Asp
65                  70                  75                  80

Lys Ile Leu Lys Asn Leu Ser Arg Asn Arg Arg Leu Val Thr Asp Lys
                85                  90                  95

Val Gly Gln Ala Cys Cys Arg Pro Ile Ala Phe Asp Asp Leu Ser
            100                 105                 110

Phe Leu Asp Asp Asn Leu Val Tyr His Ile Leu Arg Lys His Ser Ala
            115                 120                 125

Lys Arg Cys Gly Cys Ile
        130

<210> SEQ ID NO 3
<211> LENGTH: 4
<212> TYPE: PRT
<213> ORGANISM: Homo sapiens

<400> SEQUENCE: 3

Lys Asn Arg Gly
1

<210> SEQ ID NO 4
<211> LENGTH: 5
<212> TYPE: PRT
<213> ORGANISM: Homo sapiens

<400> SEQUENCE: 4

Gly Lys Asn Arg Gly
1               5

<210> SEQ ID NO 5
<211> LENGTH: 6
<212> TYPE: PRT
<213> ORGANISM: Homo sapiens

<400> SEQUENCE: 5

Arg Gly Lys Asn Arg Gly
1               5

<210> SEQ ID NO 6
<211> LENGTH: 7
<212> TYPE: PRT
<213> ORGANISM: Homo sapiens

<400> SEQUENCE: 6

Gln Arg Gly Lys Asn Arg Gly
1               5

<210> SEQ ID NO 7
<211> LENGTH: 8
<212> TYPE: PRT
<213> ORGANISM: Homo sapiens
```

```
<400> SEQUENCE: 7

Gly Gln Arg Gly Lys Asn Arg Gly
1               5

<210> SEQ ID NO 8
<211> LENGTH: 9
<212> TYPE: PRT
<213> ORGANISM: Homo sapiens

<400> SEQUENCE: 8

Arg Gly Gln Arg Gly Lys Asn Arg Gly
1               5

<210> SEQ ID NO 9
<211> LENGTH: 10
<212> TYPE: PRT
<213> ORGANISM: Homo sapiens

<400> SEQUENCE: 9

Arg Arg Gly Gln Arg Gly Lys Asn Arg Gly
1               5                   10

<210> SEQ ID NO 10
<211> LENGTH: 11
<212> TYPE: PRT
<213> ORGANISM: Homo sapiens

<400> SEQUENCE: 10

Gly Arg Arg Gly Gln Arg Gly Lys Asn Arg Gly
1               5                   10

<210> SEQ ID NO 11
<211> LENGTH: 12
<212> TYPE: PRT
<213> ORGANISM: Homo sapiens

<400> SEQUENCE: 11

Lys Gly Arg Arg Gly Gln Arg Gly Lys Asn Arg Gly
1               5                   10

<210> SEQ ID NO 12
<211> LENGTH: 13
<212> TYPE: PRT
<213> ORGANISM: Homo sapiens

<400> SEQUENCE: 12

Gly Lys Gly Arg Arg Gly Gln Arg Gly Lys Asn Arg Gly
1               5                   10

<210> SEQ ID NO 13
<211> LENGTH: 14
<212> TYPE: PRT
<213> ORGANISM: Homo sapiens

<400> SEQUENCE: 13

Arg Gly Lys Gly Arg Arg Gly Gln Arg Gly Lys Asn Arg Gly
1               5                   10

<210> SEQ ID NO 14
<211> LENGTH: 15
<212> TYPE: PRT
<213> ORGANISM: Homo sapiens

<400> SEQUENCE: 14
```

Ser Arg Gly Lys Gly Arg Arg Gly Gln Arg Gly Lys Asn Arg Gly
1               5                   10                  15

<210> SEQ ID NO 15
<211> LENGTH: 16
<212> TYPE: PRT
<213> ORGANISM: Homo sapiens

<400> SEQUENCE: 15

Asn Ser Arg Gly Lys Gly Arg Arg Gly Gln Arg Gly Lys Asn Arg Gly
1               5                   10                  15

<210> SEQ ID NO 16
<211> LENGTH: 17
<212> TYPE: PRT
<213> ORGANISM: Homo sapiens

<400> SEQUENCE: 16

Glu Asn Ser Arg Gly Lys Gly Arg Arg Gly Gln Arg Gly Lys Asn Arg
1               5                   10                  15

Gly

<210> SEQ ID NO 17
<211> LENGTH: 18
<212> TYPE: PRT
<213> ORGANISM: Homo sapiens

<400> SEQUENCE: 17

Pro Glu Asn Ser Arg Gly Lys Gly Arg Arg Gly Gln Arg Gly Lys Asn
1               5                   10                  15

Arg Gly

<210> SEQ ID NO 18
<211> LENGTH: 19
<212> TYPE: PRT
<213> ORGANISM: Homo sapiens

<400> SEQUENCE: 18

Asn Pro Glu Asn Ser Arg Gly Lys Gly Arg Arg Gly Gln Arg Gly Lys
1               5                   10                  15

Asn Arg Gly

<210> SEQ ID NO 19
<211> LENGTH: 20
<212> TYPE: PRT
<213> ORGANISM: Homo sapiens

<400> SEQUENCE: 19

Ala Asn Pro Glu Asn Ser Arg Gly Lys Gly Arg Arg Gly Gln Arg Gly
1               5                   10                  15

Lys Asn Arg Gly
            20

<210> SEQ ID NO 20
<211> LENGTH: 21
<212> TYPE: PRT
<213> ORGANISM: Homo sapiens

<400> SEQUENCE: 20

Ala Ala Asn Pro Glu Asn Ser Arg Gly Lys Gly Arg Arg Gly Gln Arg
1               5                   10                  15

Gly Lys Asn Arg Gly

-continued

<210> SEQ ID NO 21
<211> LENGTH: 22
<212> TYPE: PRT
<213> ORGANISM: Homo sapiens

<400> SEQUENCE: 21

Ala Ala Ala Asn Pro Glu Asn Ser Arg Gly Lys Gly Arg Arg Gly Gln
1               5                   10                  15

Arg Gly Lys Asn Arg Gly
            20

<210> SEQ ID NO 22
<211> LENGTH: 23
<212> TYPE: PRT
<213> ORGANISM: Homo sapiens

<400> SEQUENCE: 22

Ala Ala Ala Ala Asn Pro Glu Asn Ser Arg Gly Lys Gly Arg Arg Gly
1               5                   10                  15

Gln Arg Gly Lys Asn Arg Gly
            20

<210> SEQ ID NO 23
<211> LENGTH: 24
<212> TYPE: PRT
<213> ORGANISM: Homo sapiens

<400> SEQUENCE: 23

Gln Ala Ala Ala Ala Asn Pro Glu Asn Ser Arg Gly Lys Gly Arg Arg
1               5                   10                  15

Gly Gln Arg Gly Lys Asn Arg Gly
            20

<210> SEQ ID NO 24
<211> LENGTH: 25
<212> TYPE: PRT
<213> ORGANISM: Homo sapiens

<400> SEQUENCE: 24

Arg Gln Ala Ala Ala Ala Asn Pro Glu Asn Ser Arg Gly Lys Gly Arg
1               5                   10                  15

Arg Gly Gln Arg Gly Lys Asn Arg Gly
            20                  25

<210> SEQ ID NO 25
<211> LENGTH: 26
<212> TYPE: PRT
<213> ORGANISM: Homo sapiens

<400> SEQUENCE: 25

Asn Arg Gln Ala Ala Ala Ala Asn Pro Glu Asn Ser Arg Gly Lys Gly
1               5                   10                  15

Arg Arg Gly Gln Arg Gly Lys Asn Arg Gly
            20                  25

<210> SEQ ID NO 26
<211> LENGTH: 27
<212> TYPE: PRT
<213> ORGANISM: Homo sapiens

<400> SEQUENCE: 26

```
Arg Asn Arg Gln Ala Ala Ala Ala Asn Pro Glu Asn Ser Arg Gly Lys
 1               5                  10                  15

Gly Arg Arg Gly Gln Arg Gly Lys Asn Arg Gly
            20                  25
```

<210> SEQ ID NO 27
<211> LENGTH: 28
<212> TYPE: PRT
<213> ORGANISM: Homo sapiens

<400> SEQUENCE: 27

```
Glu Arg Asn Arg Gln Ala Ala Ala Ala Asn Pro Glu Asn Ser Arg Gly
 1               5                  10                  15 y Arg Arg Gly Gln Arg Gly Lys Asn Arg Gly
            20                  25
```

<210> SEQ ID NO 28
<211> LENGTH: 29
<212> TYPE: PRT
<213> ORGANISM: Homo sapiens

<400> SEQUENCE: 28

```
Arg Glu Arg Asn Arg Gln Ala Ala Ala Ala Asn Pro Glu Asn Ser Arg
 1               5                  10                  15

Gly Lys Gly Arg Arg Gly Gln Arg Gly Lys Asn Arg Gly
            20                  25
```

<210> SEQ ID NO 29
<211> LENGTH: 30
<212> TYPE: PRT
<213> ORGANISM: Homo sapiens

<400> SEQUENCE: 29

```
Arg Arg Glu Arg Asn Arg Gln Ala Ala Ala Ala Asn Pro Glu Asn Ser
 1               5                  10                  15

Arg Gly Lys Gly Arg Arg Gly Gln Arg Gly Lys Asn Arg Gly
            20                  25                  30
```

<210> SEQ ID NO 30
<211> LENGTH: 31
<212> TYPE: PRT
<213> ORGANISM: Homo sapiens

<400> SEQUENCE: 30

```
Pro Arg Arg Glu Arg Asn Arg Gln Ala Ala Ala Ala Asn Pro Glu Asn
 1               5                  10                  15

Ser Arg Gly Lys Gly Arg Arg Gly Gln Arg Gly Lys Asn Arg Gly
            20                  25                  30
```

<210> SEQ ID NO 31
<211> LENGTH: 32
<212> TYPE: PRT
<213> ORGANISM: Homo sapiens

<400> SEQUENCE: 31

```
Leu Pro Arg Arg Glu Arg Asn Arg Gln Ala Ala Ala Ala Asn Pro Glu
 1               5                  10                  15

Asn Ser Arg Gly Lys Gly Arg Arg Gly Gln Arg Gly Lys Asn Arg Gly
            20                  25                  30
```

<210> SEQ ID NO 32

```
<211> LENGTH: 33
<212> TYPE: PRT
<213> ORGANISM: Homo sapiens

<400> SEQUENCE: 32

Val Leu Pro Arg Arg Glu Arg Asn Arg Gln Ala Ala Ala Asn Pro
 1               5                  10                  15

Glu Asn Ser Arg Gly Lys Gly Arg Arg Gly Gln Arg Gly Lys Asn Arg
                20                  25                  30

Gly

<210> SEQ ID NO 33
<211> LENGTH: 34
<212> TYPE: PRT
<213> ORGANISM: Homo sapiens

<400> SEQUENCE: 33

Ala Val Leu Pro Arg Arg Glu Arg Asn Arg Gln Ala Ala Ala Asn
 1               5                  10                  15

Pro Glu Asn Ser Arg Gly Lys Gly Arg Arg Gly Gln Arg Gly Lys Asn
                20                  25                  30

Arg Gly

<210> SEQ ID NO 34
<211> LENGTH: 35
<212> TYPE: PRT
<213> ORGANISM: Homo sapiens

<400> SEQUENCE: 34

Met Ala Val Leu Pro Arg Arg Glu Arg Asn Arg Gln Ala Ala Ala
 1               5                  10                  15

Asn Pro Glu Asn Ser Arg Gly Lys Gly Arg Arg Gly Gln Arg Gly Lys
                20                  25                  30

Asn Arg Gly
        35

<210> SEQ ID NO 35
<211> LENGTH: 36
<212> TYPE: PRT
<213> ORGANISM: Homo sapiens

<400> SEQUENCE: 35

Gln Met Ala Val Leu Pro Arg Arg Glu Arg Asn Arg Gln Ala Ala Ala
 1               5                  10                  15

Ala Asn Pro Glu Asn Ser Arg Gly Lys Gly Arg Arg Gly Gln Arg Gly
                20                  25                  30

Lys Asn Arg Gly
        35

<210> SEQ ID NO 36
<211> LENGTH: 37
<212> TYPE: PRT
<213> ORGANISM: Homo sapiens

<400> SEQUENCE: 36

Lys Gln Met Ala Val Leu Pro Arg Arg Glu Arg Asn Arg Gln Ala Ala
 1               5                  10                  15

Ala Ala Asn Pro Glu Asn Ser Arg Gly Lys Gly Arg Arg Gly Gln Arg
                20                  25                  30

Gly Lys Asn Arg Gly
```

```
<210> SEQ ID NO 37
<211> LENGTH: 38
<212> TYPE: PRT
<213> ORGANISM: Homo sapiens

<400> SEQUENCE: 37

Asp Lys Gln Met Ala Val Leu Pro Arg Arg Glu Arg Asn Arg Gln Ala
1               5                   10                  15

Ala Ala Ala Asn Pro Glu Asn Ser Arg Gly Lys Gly Arg Arg Gly Gln
            20                  25                  30

Arg Gly Lys Asn Arg Gly
        35

<210> SEQ ID NO 38
<211> LENGTH: 39
<212> TYPE: PRT
<213> ORGANISM: Homo sapiens

<400> SEQUENCE: 38

Pro Asp Lys Gln Met Ala Val Leu Pro Arg Arg Glu Arg Asn Arg Gln
1               5                   10                  15

Ala Ala Ala Ala Asn Pro Glu Asn Ser Arg Gly Lys Gly Arg Arg Gly
            20                  25                  30

Gln Arg Gly Lys Asn Arg Gly
        35

<210> SEQ ID NO 39
<211> LENGTH: 417
<212> TYPE: DNA
<213> ORGANISM: Homo sapiens

<400> SEQUENCE: 39
catatgtctc cggataaaca aatggctgtt cttccacgtc gtgaacgtaa ccgtcaggcg      60
gccgctgcta acccggagaa ttcccgtggt aaaggtcgtc gtggtcagcg tggtaaaaac     120
cgcggttgcg ttctgaccgc tatccacctg aacgttaccg acctgggtct cggttacgaa     180
accaaagaag aattaatctt ccgttactgc tccggttcct gcgacgctgc tgaaaccacg     240
tacgacaaaa tcctgaaaaa cctgtcccgt aaccgtcgtc tggtttccga caaagttggt     300
caagcttgct gccgtccgat cgctttcgac gacgacctgt ccttcctgga cgacaacctg     360
gtttaccaca tcctgcgtaa acactccgct aagcgttgcg gttgcatcta aggatcc        417

<210> SEQ ID NO 40
<211> LENGTH: 417
<212> TYPE: DNA
<213> ORGANISM: Homo sapiens

<400> SEQUENCE: 40
catatgagcc cggacaaaca gatggcagta cttccacgtc gtgaacgtaa tcgccaggca      60
gcagctgcaa acccggaaaa ctcccgtggt aaaggtcgcc gtggccagcg cggcaaaaac     120
cgtggttgtg ttctgactgc aatccacctg aacgttactg acctgggtct gggctacgaa     180
accaaagaag aactgatctt ccgctactgc agcggctctt gcgacgcagc tgaaaccact     240
tacgacaaaa tcctgaaaaa cctgtcccgt aaccgccgtc tggtaagcga caaagtaggt     300
caggcatgct gccgtccgat cgcattcgac gatgacctga gcttcctgga tgacaacctg     360
gtttaccaca tcctgcgtaa acactccgct aaacgctgcg gttgcatcta aggatcc        417
```

<210> SEQ ID NO 41
<211> LENGTH: 345
<212> TYPE: DNA
<213> ORGANISM: Homo sapiens
<220> FEATURE:
<221> NAME/KEY: CDS
<222> LOCATION: (1)..(342)

<400> SEQUENCE: 41

| | | | | | | | | | | | | | | | | |
|---|---|---|---|---|---|---|---|---|---|---|---|---|---|---|---|---|
| atg | tcc | cca | gaa | aat | tct | cgt | ggt | aaa | ggt | cgt | cgt | ggt | cag | cgt | ggt | 48 |
| Met | Ser | Pro | Glu | Asn | Ser | Arg | Gly | Lys | Gly | Arg | Arg | Gly | Gln | Arg | Gly | |
| 1 | | | | 5 | | | | | 10 | | | | | 15 | | |
| aat | aac | cgc | ggt | tgc | gtt | ctg | acc | gct | atc | cac | ctg | aac | gtt | acc | gac | 96 |
| Asn | Asn | Arg | Gly | Cys | Val | Leu | Thr | Ala | Ile | His | Leu | Asn | Val | Thr | Asp | |
| | | | 20 | | | | | 25 | | | | | 30 | | | |
| ctg | ggt | ctc | ggt | tac | gaa | acc | aaa | gaa | gaa | tta | atc | ttc | cgt | tac | tgc | 144 |
| Leu | Gly | Leu | Gly | Tyr | Glu | Thr | Lys | Glu | Glu | Leu | Ile | Phe | Arg | Tyr | Cys | |
| | | | 35 | | | | | 40 | | | | | 45 | | | |
| tcc | ggt | tcc | tgc | gac | gct | gct | gaa | acc | acg | tac | gac | aaa | atc | ctg | aaa | 192 |
| Ser | Gly | Ser | Cys | Asp | Ala | Ala | Glu | Thr | Thr | Tyr | Asp | Lys | Ile | Leu | Lys | |
| | 50 | | | | | 55 | | | | | 60 | | | | | |
| aac | ctg | tcc | cgt | aac | cgt | cgt | ctg | gtt | tcc | gac | aaa | gtt | ggt | caa | gct | 240 |
| Asn | Leu | Ser | Arg | Asn | Arg | Arg | Leu | Val | Ser | Asp | Lys | Val | Gly | Gln | Ala | |
| 65 | | | | | 70 | | | | | 75 | | | | | 80 | |
| tgc | tgc | cgt | ccg | atc | gct | ttc | gac | gac | gac | ctg | tcc | ttc | ctg | gac | gac | 288 |
| Cys | Cys | Arg | Pro | Ile | Ala | Phe | Asp | Asp | Asp | Leu | Ser | Phe | Leu | Asp | Asp | |
| | | | | 85 | | | | | 90 | | | | | 95 | | |
| aac | ctg | gtt | tac | cac | atc | ctg | cgt | aaa | cac | tcc | gct | aag | cgt | tgc | ggt | 336 |
| Asn | Leu | Val | Tyr | His | Ile | Leu | Arg | Lys | His | Ser | Ala | Lys | Arg | Cys | Gly | |
| | | | 100 | | | | | 105 | | | | | 110 | | | |
| tgc | atc | taa | | | | | | | | | | | | | | 345 |
| Cys | Ile | | | | | | | | | | | | | | | |

<210> SEQ ID NO 42
<211> LENGTH: 114
<212> TYPE: PRT
<213> ORGANISM: Homo sapiens

<400> SEQUENCE: 42

Met Ser Pro Glu Asn Ser Arg Gly Lys Gly Arg Arg Gly Gln Arg Gly
1               5                   10                  15

Asn Asn Arg Gly Cys Val Leu Thr Ala Ile His Leu Asn Val Thr Asp
            20                  25                  30

Leu Gly Leu Gly Tyr Glu Thr Lys Glu Glu Leu Ile Phe Arg Tyr Cys
        35                  40                  45

Ser Gly Ser Cys Asp Ala Ala Glu Thr Thr Tyr Asp Lys Ile Leu Lys
    50                  55                  60

Asn Leu Ser Arg Asn Arg Arg Leu Val Ser Asp Lys Val Gly Gln Ala
65                  70                  75                  80

Cys Cys Arg Pro Ile Ala Phe Asp Asp Asp Leu Ser Phe Leu Asp Asp
                85                  90                  95

Asn Leu Val Tyr His Ile Leu Arg Lys His Ser Ala Lys Arg Cys Gly
            100                 105                 110

Cys Ile

<210> SEQ ID NO 43
<211> LENGTH: 315
<212> TYPE: DNA
<213> ORGANISM: Homo sapiens

```
<220> FEATURE:
<221> NAME/KEY: CDS
<222> LOCATION: (1)..(312)

<400> SEQUENCE: 43 atg cgt ggt caa cgt ggt aaa aac cgc ggt tgc gtt ctg act gca atc          48
Met Arg Gly Gln Arg Gly Lys Asn Arg Gly Cys Val Leu Thr Ala Ile
1               5                   10                  15 cac ctg aac gtt act gac ctg ggt ctg ggc tac gaa acc aaa gaa gaa          96
His Leu Asn Val Thr Asp Leu Gly Leu Gly Tyr Glu Thr Lys Glu Glu
                20                  25                  30 ctg atc ttc cgc tac tgc agc ggc tct tgc gac gca gct gaa acc act         144
Leu Ile Phe Arg Tyr Cys Ser Gly Ser Cys Asp Ala Ala Glu Thr Thr
            35                  40                  45 tac gac aaa atc ctg aaa aac ctg tcc cgt aac cgc cgt ctg gta agc         192
Tyr Asp Lys Ile Leu Lys Asn Leu Ser Arg Asn Arg Arg Leu Val Ser
        50                  55                  60 gac aaa gta ggt cag gca tgc tgc cgt ccg atc gca ttc gac gat gac         240
Asp Lys Val Gly Gln Ala Cys Cys Arg Pro Ile Ala Phe Asp Asp Asp
65                  70                  75                  80 ctg agc ttc ctg gat gac aac ctg gtt tac cac atc ctg cgt aaa cac         288
Leu Ser Phe Leu Asp Asp Asn Leu Val Tyr His Ile Leu Arg Lys His
                85                  90                  95 tcc gct aaa cgc tgc ggt tgc atc taa                                     315
Ser Ala Lys Arg Cys Gly Cys Ile
            100

<210> SEQ ID NO 44
<211> LENGTH: 104
<212> TYPE: PRT
<213> ORGANISM: Homo sapiens

<400> SEQUENCE: 44

Met Arg Gly Gln Arg Gly Lys Asn Arg Gly Cys Val Leu Thr Ala Ile
1               5                   10                  15

His Leu Asn Val Thr Asp Leu Gly Leu Gly Tyr Glu Thr Lys Glu Glu
                20                  25                  30

Leu Ile Phe Arg Tyr Cys Ser Gly Ser Cys Asp Ala Ala Glu Thr Thr
            35                  40                  45

Tyr Asp Lys Ile Leu Lys Asn Leu Ser Arg Asn Arg Arg Leu Val Ser
        50                  55                  60

Asp Lys Val Gly Gln Ala Cys Cys Arg Pro Ile Ala Phe Asp Asp Asp
65                  70                  75                  80

Leu Ser Phe Leu Asp Asp Asn Leu Val Tyr His Ile Leu Arg Lys His
                85                  90                  95

Ser Ala Lys Arg Cys Gly Cys Ile
            100

<210> SEQ ID NO 45
<211> LENGTH: 312
<212> TYPE: DNA
<213> ORGANISM: Homo sapiens
<220> FEATURE:
<221> NAME/KEY: CDS
<222> LOCATION: (1)..(309)

<400> SEQUENCE: 45 atg ggt caa cgt ggt aaa aac cgt ggt tgt gtt ctg act gca atc cac          48
Met Gly Gln Arg Gly Lys Asn Arg Gly Cys Val Leu Thr Ala Ile His
1               5                   10                  15 ctg aac gtt act gac ctg ggt ctg ggc tac gaa acc aaa gaa gaa ctg          96
```

```
Leu Asn Val Thr Asp Leu Gly Leu Gly Tyr Glu Thr Lys Glu Glu Leu
            20                  25                  30 atc ttc cgc tac tgc agc ggc tct tgc gac gca gct gaa acc act tac    144
Ile Phe Arg Tyr Cys Ser Gly Ser Cys Asp Ala Ala Glu Thr Thr Tyr
        35                  40                  45 gac aaa atc ctg aaa aac ctg tcc cgt aac cgc cgt ctg gta agc gac    192
Asp Lys Ile Leu Lys Asn Leu Ser Arg Asn Arg Arg Leu Val Ser Asp
 50                  55                  60 aaa gta ggt cag gca tgc tgc cgt ccg atc gca ttc gac gat gac ctg    240
Lys Val Gly Gln Ala Cys Cys Arg Pro Ile Ala Phe Asp Asp Asp Leu
65                  70                  75                  80 agc ttc ctg gat gac aac ctg gtt tac cac atc ctg cgt aaa cac tcc    288
Ser Phe Leu Asp Asp Asn Leu Val Tyr His Ile Leu Arg Lys His Ser
                85                  90                  95 gct aaa cgc tgc ggt tgc atc taa                                    312
Ala Lys Arg Cys Gly Cys Ile
            100
```

```
<210> SEQ ID NO 46
<211> LENGTH: 103
<212> TYPE: PRT
<213> ORGANISM: Homo sapiens

<400> SEQUENCE: 46

Met Gly Gln Arg Gly Lys Asn Arg Gly Cys Val Leu Thr Ala Ile His
1               5                   10                  15

Leu Asn Val Thr Asp Leu Gly Leu Gly Tyr Glu Thr Lys Glu Glu Leu
            20                  25                  30

Ile Phe Arg Tyr Cys Ser Gly Ser Cys Asp Ala Ala Glu Thr Thr Tyr
        35                  40                  45

Asp Lys Ile Leu Lys Asn Leu Ser Arg Asn Arg Arg Leu Val Ser Asp
 50                  55                  60

Lys Val Gly Gln Ala Cys Cys Arg Pro Ile Ala Phe Asp Asp Asp Leu
65                  70                  75                  80

Ser Phe Leu Asp Asp Asn Leu Val Tyr His Ile Leu Arg Lys His Ser
                85                  90                  95

Ala Lys Arg Cys Gly Cys Ile
            100
```

```
<210> SEQ ID NO 47
<211> LENGTH: 135
<212> TYPE: PRT
<213> ORGANISM: Homo sapiens

<400> SEQUENCE: 47

Met Ser Pro Asp Lys Gln Met Ala Val Leu Pro Arg Arg Glu Arg Asn
1               5                   10                  15

Arg Gln Ala Ala Ala Ala Asn Pro Glu Asn Ser Arg Gly Lys Gly Arg
            20                  25                  30

Arg Gly Gln Arg Gly Lys Asn Arg Gly Cys Val Leu Thr Ala Ile His
        35                  40                  45

Leu Asn Val Thr Asp Leu Gly Leu Gly Tyr Glu Thr Lys Glu Glu Leu
    50                  55                  60

Ile Phe Arg Tyr Cys Ser Gly Ser Cys Asp Ala Ala Glu Thr Thr Tyr
65                  70                  75                  80

Asp Lys Ile Leu Lys Asn Leu Ser Arg Asn Arg Arg Leu Val Ser Asp
                85                  90                  95

Lys Val Gly Gln Ala Cys Cys Arg Pro Ile Ala Phe Asp Asp Asp Leu
```

```
                    100                 105                 110
Ser Phe Leu Asp Asp Asn Leu Val Tyr His Ile Leu Arg Lys His Ser
            115                 120                 125
Ala Lys Arg Cys Gly Cys Ile
        130                 135

<210> SEQ ID NO 48
<211> LENGTH: 104
<212> TYPE: PRT
<213> ORGANISM: Homo sapiens

<400> SEQUENCE: 48

Met Arg Gly Gln Arg Gly Lys Asn Arg Gly Cys Val Leu Thr Ala Ile
1               5                   10                  15

His Leu Asn Val Thr Asp Leu Gly Leu Gly Tyr Glu Thr Lys Glu Glu
            20                  25                  30

Leu Ile Phe Arg Tyr Cys Ser Gly Ser Cys Asp Ala Ala Glu Thr Thr
        35                  40                  45

Tyr Asp Lys Ile Leu Lys Asn Leu Ser Arg Asn Arg Arg Leu Val Ser
    50                  55                  60

Asp Lys Val Gly Gln Ala Cys Cys Arg Pro Ile Ala Phe Asp Asp Asp
65                  70                  75                  80

Leu Ser Phe Leu Asp Asp Asn Leu Val Tyr His Ile Leu Arg Lys His
                85                  90                  95

Ser Ala Lys Arg Cys Gly Cys Ile
            100

<210> SEQ ID NO 49
<211> LENGTH: 103
<212> TYPE: PRT
<213> ORGANISM: Homo sapiens

<400> SEQUENCE: 49

Met Gly Gln Arg Gly Lys Asn Arg Gly Cys Val Leu Thr Ala Ile His
1               5                   10                  15

Leu Asn Val Thr Asp Leu Gly Leu Gly Tyr Glu Thr Lys Glu Glu Leu
            20                  25                  30

Ile Phe Arg Tyr Cys Ser Gly Ser Cys Asp Ala Ala Glu Thr Thr Tyr
        35                  40                  45

Asp Lys Ile Leu Lys Asn Leu Ser Arg Asn Arg Arg Leu Val Ser Asp
    50                  55                  60

Lys Val Gly Gln Ala Cys Cys Arg Pro Ile Ala Phe Asp Asp Asp Leu
65                  70                  75                  80

Ser Phe Leu Asp Asp Asn Leu Val Tyr His Ile Leu Arg Lys His Ser
                85                  90                  95

Ala Lys Arg Cys Gly Cys Ile
            100

<210> SEQ ID NO 50
<211> LENGTH: 114
<212> TYPE: PRT
<213> ORGANISM: Homo sapiens

<400> SEQUENCE: 50

Met Ser Pro Glu Asn Ser Arg Gly Lys Gly Arg Gly Gln Arg Gly
1               5                   10                  15

Asn Asn Arg Gly Cys Val Leu Thr Ala Ile His Leu Asn Val Thr Asp
            20                  25                  30
```

```
Leu Gly Leu Gly Tyr Glu Thr Lys Glu Leu Ile Phe Arg Tyr Cys
            35                  40                  45

Ser Gly Ser Cys Asp Ala Ala Glu Thr Thr Tyr Asp Lys Ile Leu Lys
    50                  55                  60

Asn Leu Ser Arg Asn Arg Arg Leu Val Ser Asp Lys Val Gly Gln Ala
65                  70                  75                  80

Cys Cys Arg Pro Ile Ala Phe Asp Asp Asp Leu Ser Phe Leu Asp Asp
                85                  90                  95

Asn Leu Val Tyr His Ile Leu Arg Lys His Ser Ala Lys Arg Cys Gly
            100                 105                 110

Cys Ile

<210> SEQ ID NO 51
<211> LENGTH: 19
<212> TYPE: PRT
<213> ORGANISM: Homo sapiens

<400> SEQUENCE: 51

Ser Pro Glu Asn Ser Arg Gly Lys Gly Arg Arg Gly Gln Arg Gly Lys
1               5                   10                  15

Asn Arg Gly
```